(12) United States Patent
Viola

(10) Patent No.: US 8,910,846 B2
(45) Date of Patent: Dec. 16, 2014

(54) GEAR DRIVEN KNIFE DRIVE MECHANISM

(75) Inventor: Frank J. Viola, Sandy Hook, CT (US)

(73) Assignee: Covidien LP, Mansfield, MA (US)

(*) Notice: Subject to any disclaimer, the term of this patent is extended or adjusted under 35 U.S.C. 154(b) by 1890 days.

(21) Appl. No.: 11/804,104

(22) Filed: May 17, 2007

(65) Prior Publication Data

US 2008/0287977 A1  Nov. 20, 2008

(51) Int. Cl.
*A61B 17/04* (2006.01)
*A61B 17/072* (2006.01)
*A61B 17/29* (2006.01)
*A61B 17/00* (2006.01)

(52) U.S. Cl.
CPC ... *A61B 17/07207* (2013.01); *A61B 2017/2934* (2013.01); *A61B 2017/2927* (2013.01); *A61B 2017/00685* (2013.01); *A61B 2017/2943* (2013.01)
USPC ...................................... 227/175.1

(58) Field of Classification Search
USPC ................. 606/185, 151; 227/175.1
See application file for complete search history.

(56) References Cited

U.S. PATENT DOCUMENTS

| | | | |
|---|---|---|---|
| 5,085,663 A | | 2/1992 | Tarr |
| 5,281,220 A | * | 1/1994 | Blake, III ...................... 606/46 |
| 5,330,502 A | * | 7/1994 | Hassler et al. ................ 606/205 |
| 5,827,279 A | | 10/1998 | Hughett et al. |
| 5,830,221 A | * | 11/1998 | Stein et al. .................... 606/157 |
| 6,953,139 B2 | * | 10/2005 | Milliman et al. ........... 227/175.1 |
| 7,134,587 B2 | | 11/2006 | Schwemberger et al. |
| 7,150,749 B2 | | 12/2006 | Dycus et al. |
| 7,189,207 B2 | | 3/2007 | Viola |
| 7,207,472 B2 | | 4/2007 | Wukusick et al. |
| 2007/0023477 A1 | * | 2/2007 | Whitman et al. .......... 227/175.1 |
| 2007/0039997 A1 | * | 2/2007 | Mather et al. .............. 227/176.1 |

* cited by examiner

*Primary Examiner* — Gregory Anderson
*Assistant Examiner* — Christina Lauer

(57) ABSTRACT

A surgical apparatus includes a handle assembly, an elongated body portion defining a first longitudinal axis, a tool assembly pivotally supported on the distal end of the elongated body portion to form a pivot axis, and a flexible drive assembly that includes a flexible drive member extending from a position proximal of the pivot axis to a position distal of the pivot axis. The drive member has a distal end which is movable in relation to the tool assembly and a gear drive assembly to enable movement of the distal end of the flexible drive member. The flexible drive assembly includes a flexible knife drive beam that advances or retracts via a primary drive gear meshing with the flexible knife drive beam to effect movement of the flexible knife drive beam.

17 Claims, 27 Drawing Sheets

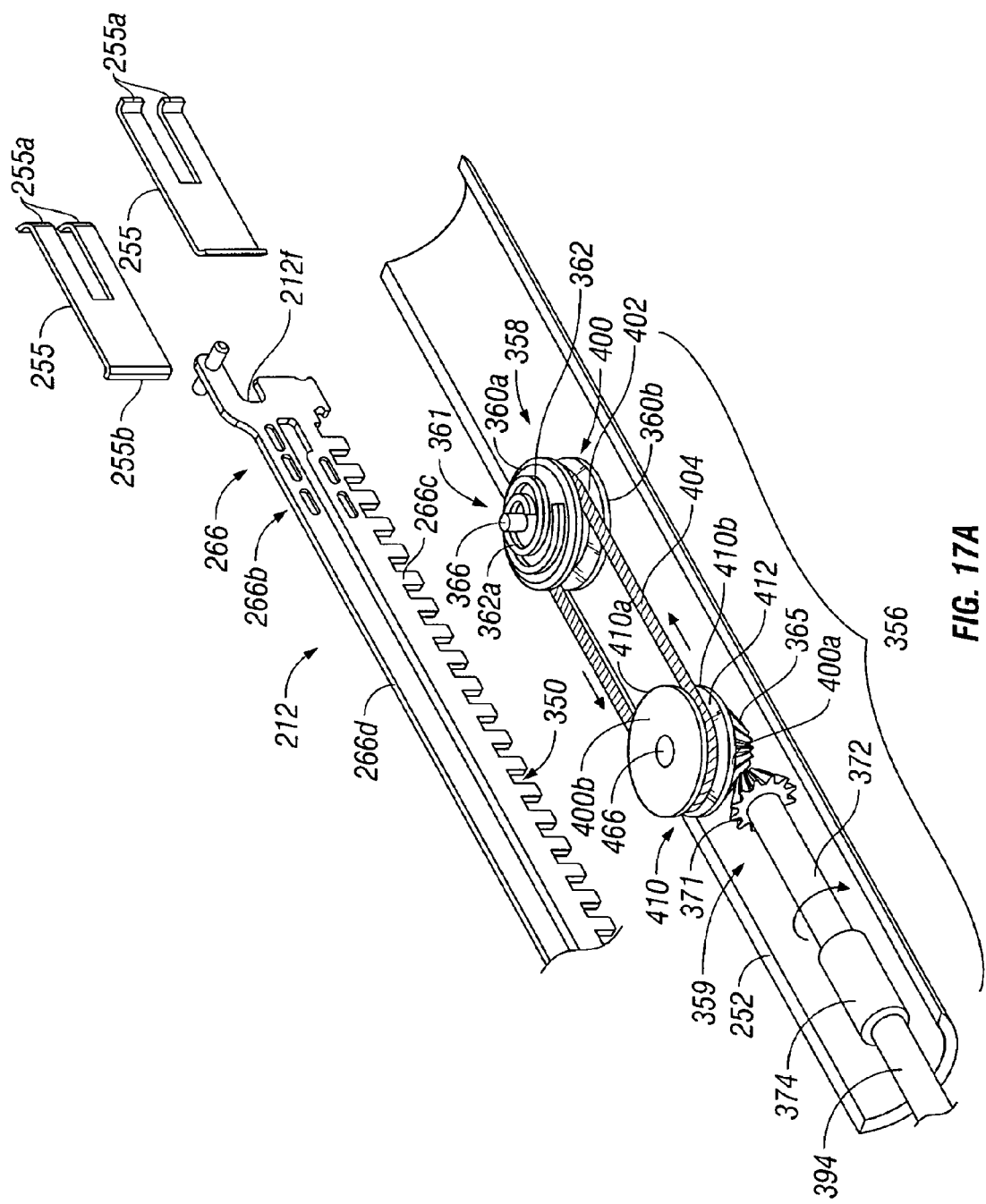

GEAR DRIVEN KNIFE DRIVE MECHANISM

BACKGROUND

1. Technical Field

This application relates to a surgical apparatus, and more particularly, to an articulating mechanism for use with an endoscopic surgical stapling apparatus for applying a plurality of surgical fasteners to body tissue and optionally incising fastened tissue.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

However, existing surgical instruments do not provide at least one-directional articulation of about 90 degrees without sacrificing the existing important benefits of the surgical instrument.

SUMMARY

To address the issues described above with respect to surgical stapling apparatuses of the prior art, the present disclosure relates to a surgical apparatus that includes a handle assembly, an elongated body portion extending distally from the handle assembly and defining a first longitudinal axis, a tool assembly pivotally supported on the distal end of the elongated body portion about a pivot axis substantially orthogonal to the first longitudinal axis, with the tool assembly defining a second longitudinal axis and being movable between a first position in which the second longitudinal axis is aligned with the first longitudinal axis to a second position in which the second longitudinal axis is positioned at an angle to the first longitudinal axis, and a flexible drive assembly that includes a flexible drive member extending from a position proximal of the pivot axis to a position distal of the pivot axis. The drive member has a distal end which is movable in relation to the tool assembly to actuate the tool assembly. The flexible drive assembly also includes a gear drive assembly interfacing with the flexible drive member to enable movement of the distal end of the flexible drive member in relation to the tool assembly.

The movement of the distal end of the flexible drive member in relation to the tool assembly may be effected independently of the movement of the tool assembly between the first position in which the second longitudinal axis is aligned with the first longitudinal axis to the second position in which the second longitudinal axis is positioned at an angle to the first longitudinal axis. In addition, the flexible drive assembly may include a flexible knife drive beam, with the flexible knife drive beam at least one of advancing and retracting at a distal end thereof to effect the movement of the flexible drive member in relation to the tool assembly. The gear drive assembly may include a primary drive gear meshing with the flexible knife drive beam to effect the movement of the flexible drive member. The primary drive gear may be either driven directly by a rotating shaft or driven by various secondary drive gears.

BRIEF DESCRIPTION OF THE DRAWINGS

Various embodiments of the presently disclosed surgical apparatus are described herein with reference to the drawings, wherein:

FIG. 17A is a perspective view of the axial drive assembly of FIG. 17 for the disposable loading unit with parts separated;

DETAILED DESCRIPTION

Figure 1:
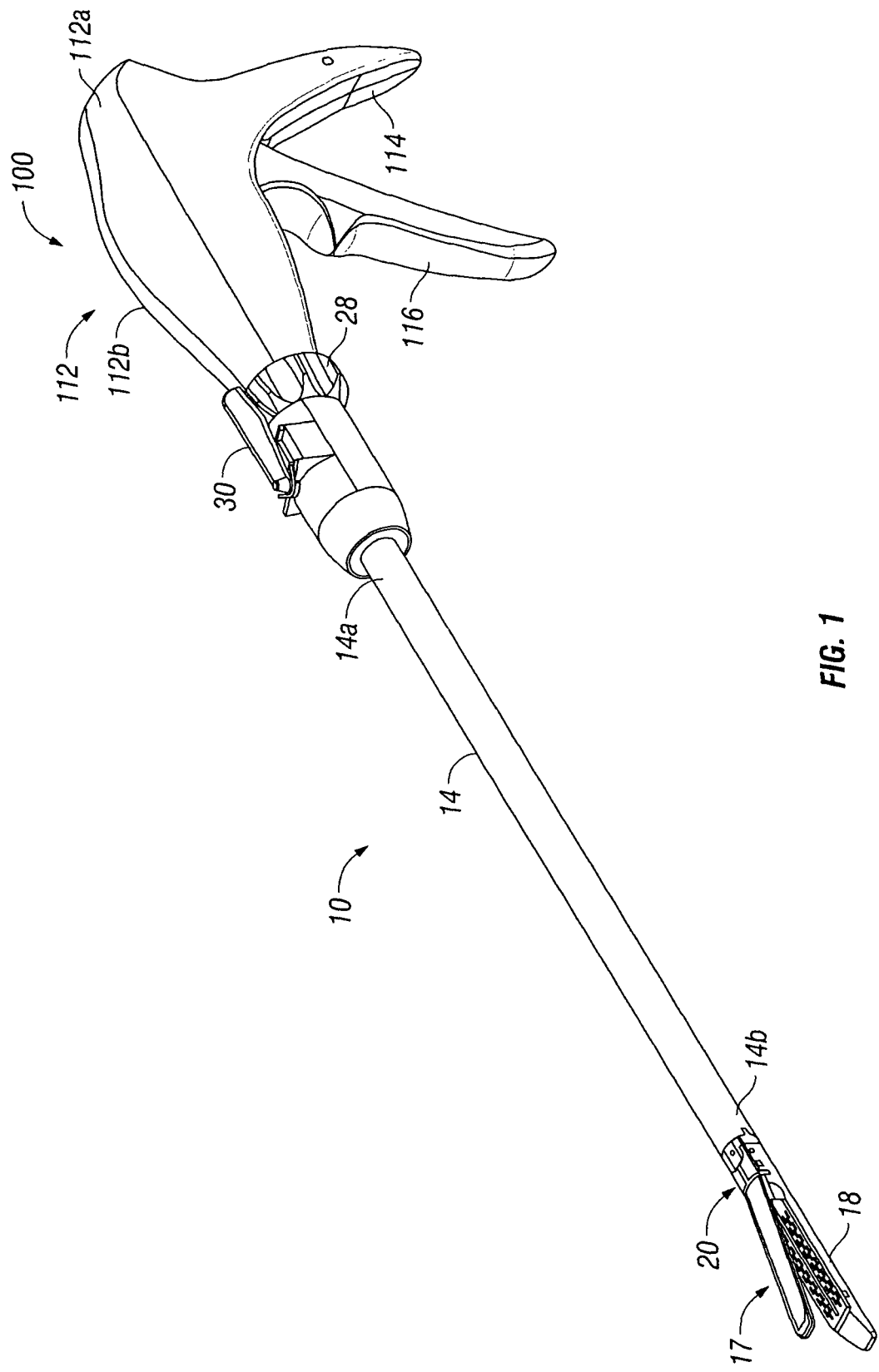
FIG. 1 is a perspective view of an embodiment of the presently disclosed surgical stapling apparatus.

Embodiments of the presently disclosed endoscopic surgical stapling apparatus will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term distal will refer to the end of the apparatus which is furthest from the operator.

Referring now to FIGS. 1-4, a surgical stapling apparatus for applying surgical staples is shown generally as surgical stapling apparatus 10. Surgical stapling apparatus 10 generally includes a handle assembly 100. The handle assembly 100 includes proximal housing portion 112, which may be formed as two separate housing halves 112a and 112b and a handle portion 114 extending from housing portion 112. The handle assembly 100 includes a trigger 116 that is movably mounted to housing 112. Trigger 116 may be pivotally connected to housing 112 and biased toward a position in which a free end of trigger 116 is spaced from a free end of handle portion 114. This arrangement provides an ergonomic advantage and positive secure control of trigger 116 and surgical stapling apparatus 10. The trigger 116 forms a portion of a driver/torque subassembly 120.

Figure 4:
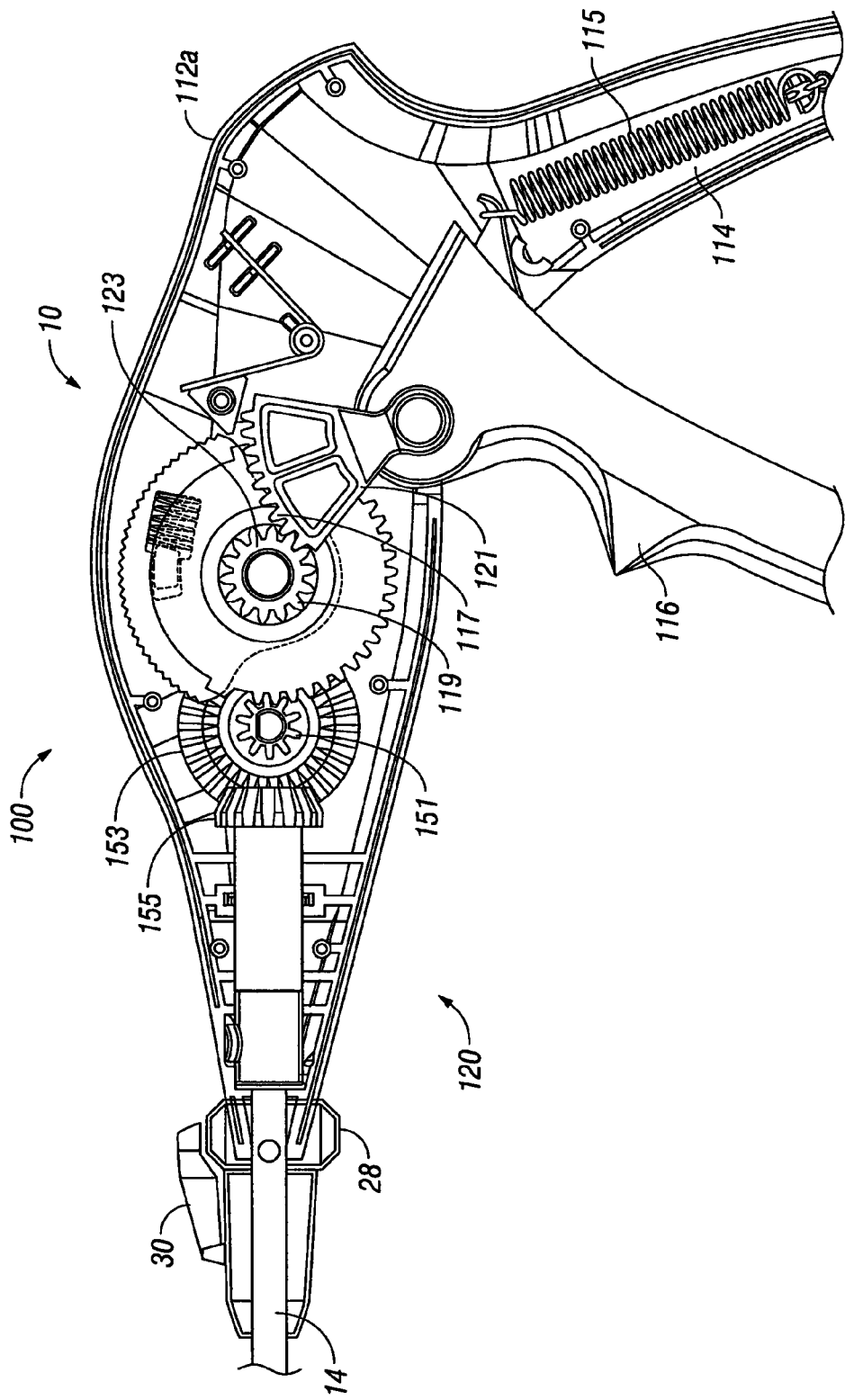
FIG. 4 is a side view, partially in section, of the housing portion of the surgical apparatus of FIG. 1 showing an initial position.

With continued reference to FIG. 4, operation of the driver/torque subassembly 120 of housing portion 112 of surgical stapling apparatus 100 is described. In an initial or starting position, trigger 116 is biased away from handle 114 due to the force of return spring 115. As shown, the driver/torque subassembly 120 includes teeth 117 of gear portion 121 of trigger 116 that are engaged with teeth 119 of trigger gear 123. As trigger 116 is squeezed, teeth 117 engage teeth 119 of trigger gear 123 to rotate driver gear 151, which, in turn, rotates a first bevel gear 153 which, in turn, rotates a bevel drive gear 155 and ultimately a drive gear shaft as discussed below. Reference may be made to commonly assigned U.S. Pat. No. 5,830,221 by Stein et al., the entire contents of which are incorporated herein by reference, for a detailed discussion of the operation of a driver/torque subassembly that may be used for a surgical stapling apparatus 10 according to the present disclosure. The drive gear shaft may also be driven by a motor connected to a power source that is external or internal to the surgical stapling apparatus 10.

Figure 2:
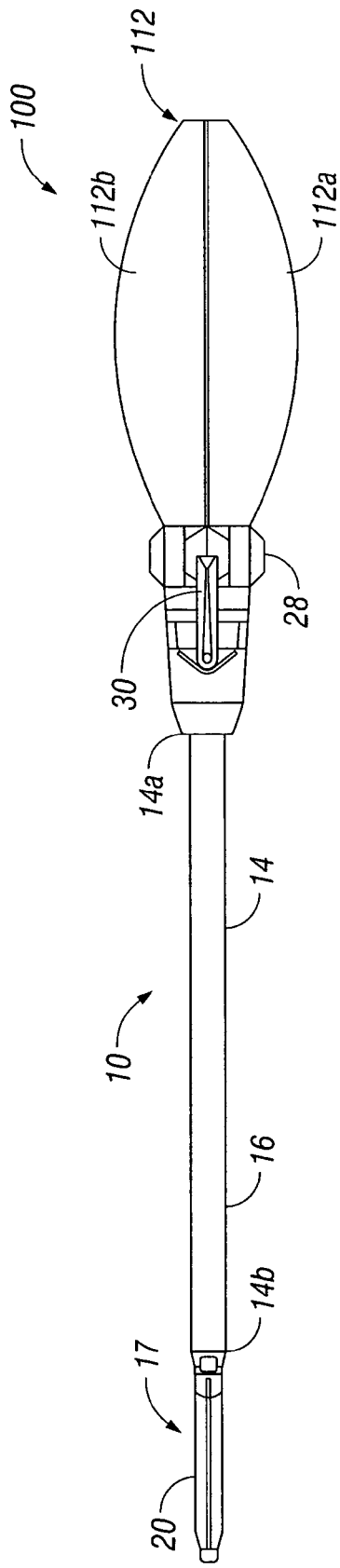
FIG. 2 is a top view of the surgical apparatus shown in FIG. 1.
Figure 3:
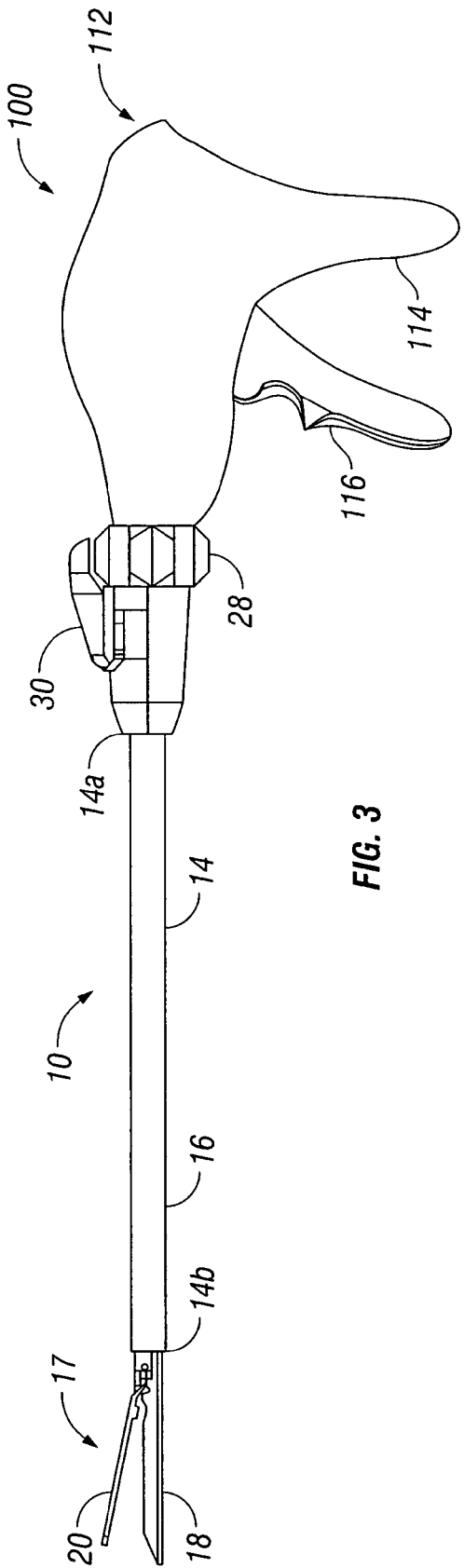
FIG. 3 is a side view of the surgical apparatus shown in FIG. 1.

In conjunction with FIGS. 2 and 3, the surgical stapling apparatus 10 includes an elongated body 14 operatively coupled to the housing assembly 112. The elongated body 14 has proximal and distal ends 14a and 14b, respectively, defining a longitudinal axis and is configured to enclose an articulation bar 390 (FIG. 14) and a rotatable shaft 394 (FIG. 14), with the articulation bar 390 and the shaft 394 having appropriate bearing structures, e.g., a sleeve bearing disposed therebetween such that the articulation bar 390 and the rotatable shaft 394 may be each moved independently without interfering with one another. In one embodiment, an articulation lever 30 is mounted on the forward end of housing assembly 112 to facilitate articulation of tool assembly 17. The surgical stapling apparatus 10 has the tool assembly 17 with a cartridge assembly 18 housing a plurality of surgical staples and an anvil assembly 20 movably secured in relation to cartridge assembly 18. The elongate body 14 extends from the housing assembly 112 at the proximal end 14a to the tool assembly 17 at the distal end 14b. The tool assembly 17 is configured to apply linear rows of staples measuring from about 30 mm to about 60 mm in length. Disposable loading units having linear rows of staples of other lengths are also envisioned, e.g., 45 mm.

The general overall arrangement, construction and operation of surgical stapling apparatus 10 is similar in many respects to surgical stapling apparatuses such as, for example but not limited to, that described in more detail in commonly assigned U.S. Pat. No. 6,953,139 B2, by Milliman et al, published Oct. 11, 2005, the entire contents of which is incorporated by reference herein. However, as described in more detail below, the surgical stapling apparatus 10 disclosed herein effects articulation of the tool assembly 17 and independent rotation of a shaft to advance or retract a knife drive beam. It is contemplated also that the surgical stapling apparatus 10 may be configured as an articulatable surgical stapling apparatus having a disposable loading unit as described in the aforementioned U.S. Pat. No. 6,953,139 B2.

Referring to FIGS. 5-13, in one embodiment, tool assembly 17 includes anvil assembly 20 and cartridge assembly 18. Anvil assembly 20 includes anvil portion 204 having a plurality of staple deforming concavities 206 (FIG. 9) and a cover plate 208 secured to a top surface of anvil portion 204 to define a cavity 210 (FIG. 11) therebetween. Cover plate 208 is provided to prevent pinching of tissue during clamping and firing of stapling apparatus 10. Cavity 210 is dimensioned to receive a distal end of a flexible axial drive assembly 212 (see FIGS. 14, 16, 17 and 18). A longitudinal slot 214 extends through anvil portion 204 to facilitate passage of retention flange 284 (see FIGS. 14, 16, 17 and 18) of flexible axial drive assembly 212 into the anvil cavity 210. A camming surface 209 formed on anvil portion 204 is positioned to engage flexible axial drive assembly 212 to facilitate clamping of tissue 198. A pair of pivot members 211 formed on anvil portion 204 are positioned within slots 213 formed in carrier 216 to guide the anvil portion between the open and clamped positions.

Cartridge assembly 18 includes the carrier 216 which defines an elongated support channel 218. Elongated support channel 218 is dimensioned and configured to receive a staple cartridge 220. Corresponding tabs 222 and slots 224 formed along staple cartridge 220 and elongated support channel 218 function to retain staple cartridge 220 within support channel 218. A pair of support struts 223 formed on staple cartridge 220 is positioned to rest on side walls of carrier 216 to further stabilize staple cartridge 220 within support channel 218.

Staple cartridge 220 includes retention slots 225 for receiving a plurality of fasteners 226 and pushers 228. A plurality of spaced apart longitudinal slots 230 extends through staple cartridge 220 to accommodate upstanding cam wedges 232 of actuation sled 234. A central longitudinal slot 282 extends along the length of staple cartridge 220 to facilitate passage of a knife blade 280. During operation of surgical stapler 10, actuation sled 234 translates through longitudinal slots 230 of staple cartridge 220 to advance cam wedges 232 into sequential contact with pushers 228, to cause pushers 228 to translate vertically within slots 224 and urge fasteners 226 from slots 224 into the staple deforming cavities 206 of anvil assembly 20.

Referring to FIGS. 7, 8, 14, 14A, 14B, 14C, 15, 16, 16A, 16B and 16C, mounting assembly 202 includes upper and lower mounting portions 236 and 238. Each mounting portion includes a threaded bore 240 on each side thereof dimensioned to receive threaded bolts 242 (see FIG. 8) for securing the proximal end of carrier 216 thereto. A pair of centrally located pivot members 244 (see FIG. 8) extends between upper and lower mounting portions via a pair of coupling members 246 which engage the distal end of housing portion 200.

Figure 14:
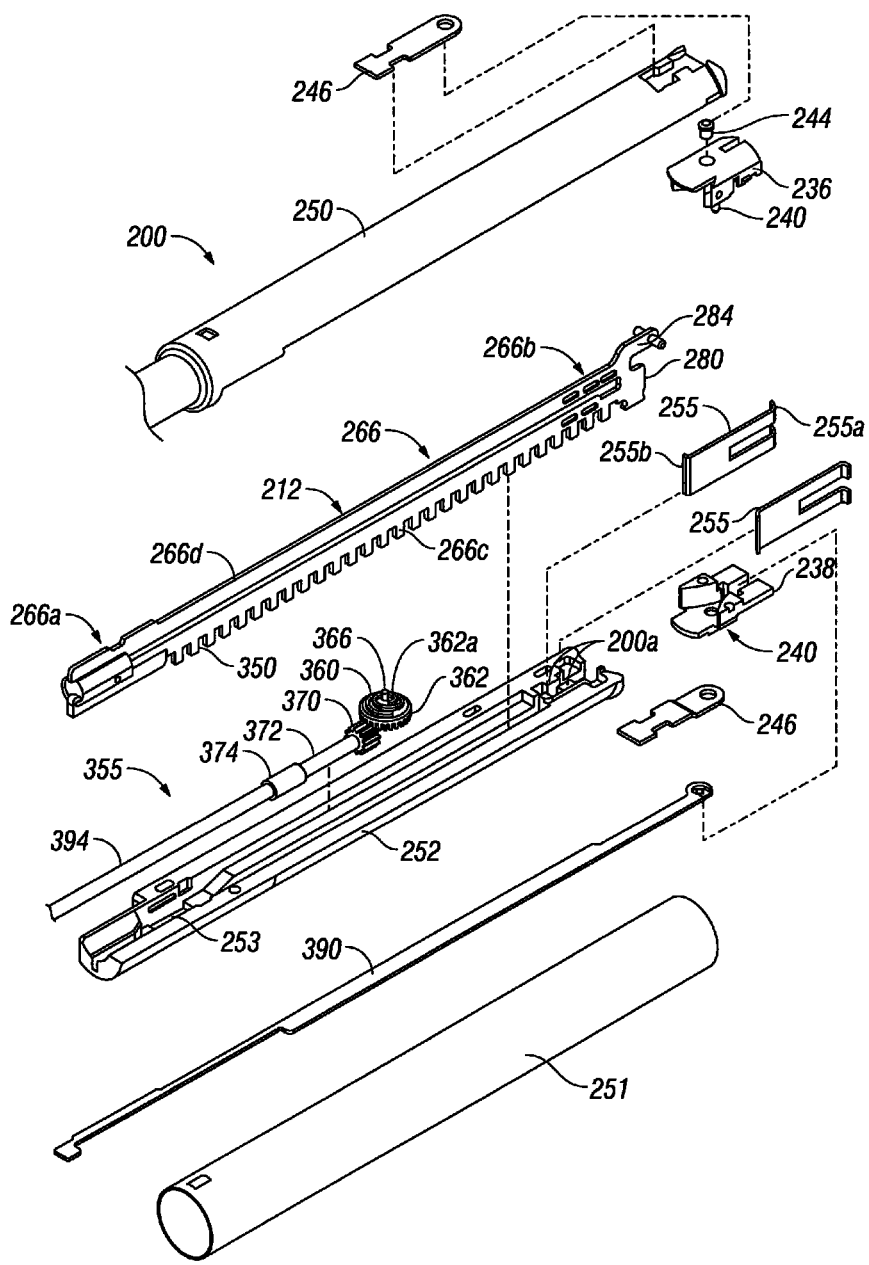
FIG. 14 is an enlarged perspective view with parts separated of the proximal housing portion and mounting assembly of the disposable loading unit shown in FIG. 6.
Figure 14A:
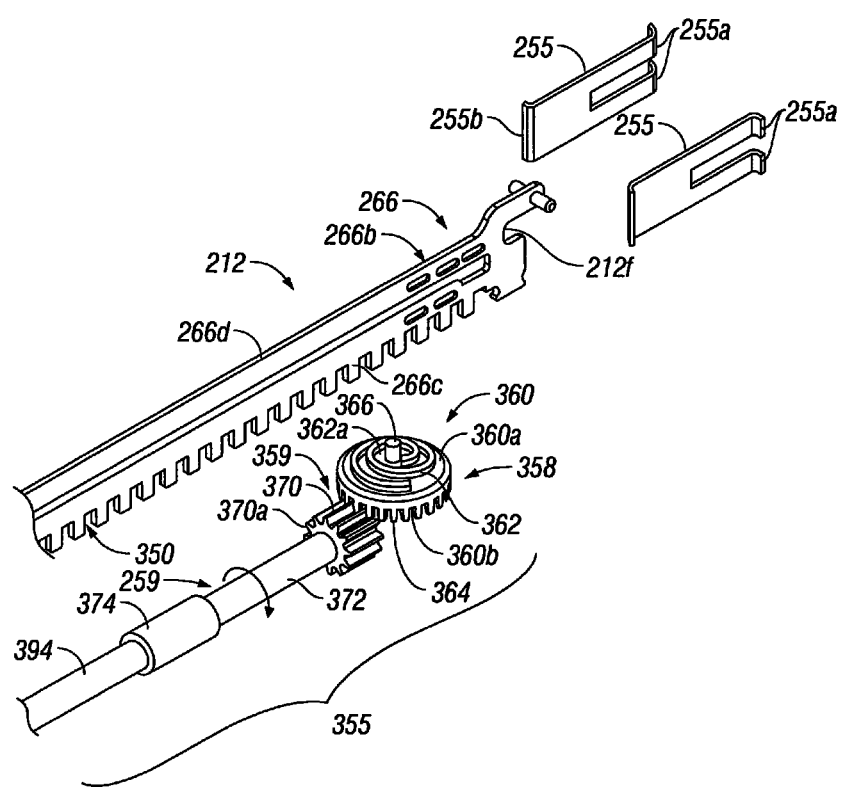
FIG. 14A is a perspective view of an axial drive assembly for the disposable loading unit shown in FIG. 6 with parts separated.
Figure 14B:
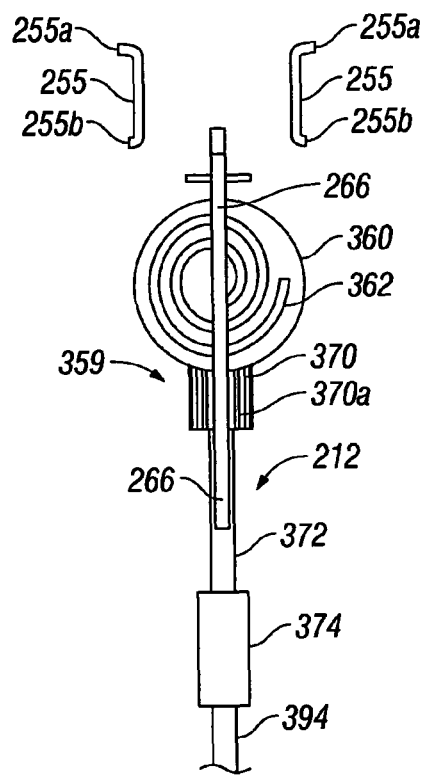
FIG. 14B is a plan view of the axial drive assembly shown in FIG. 14A.
Figure 14C:
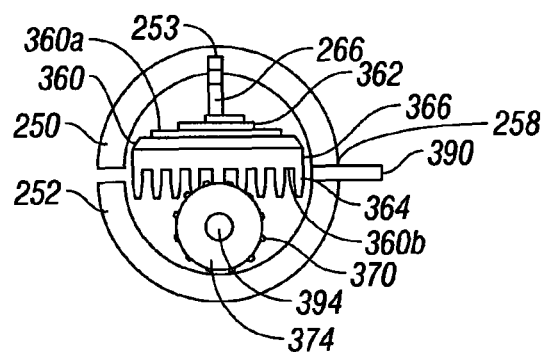
FIG. 14C is a cross-sectional view of the disposable loading unit taken along section line 14C-14C of FIGS. 6 and 7.
Figure 15:
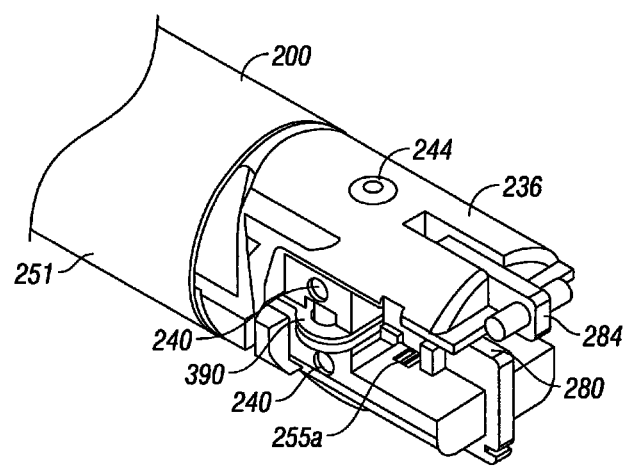
FIG. 15 is an enlarged perspective view of the mounting assembly of the disposable loading unit shown in FIG. 6 mounted to a distal end portion of the proximal housing portion.
Figure 16:
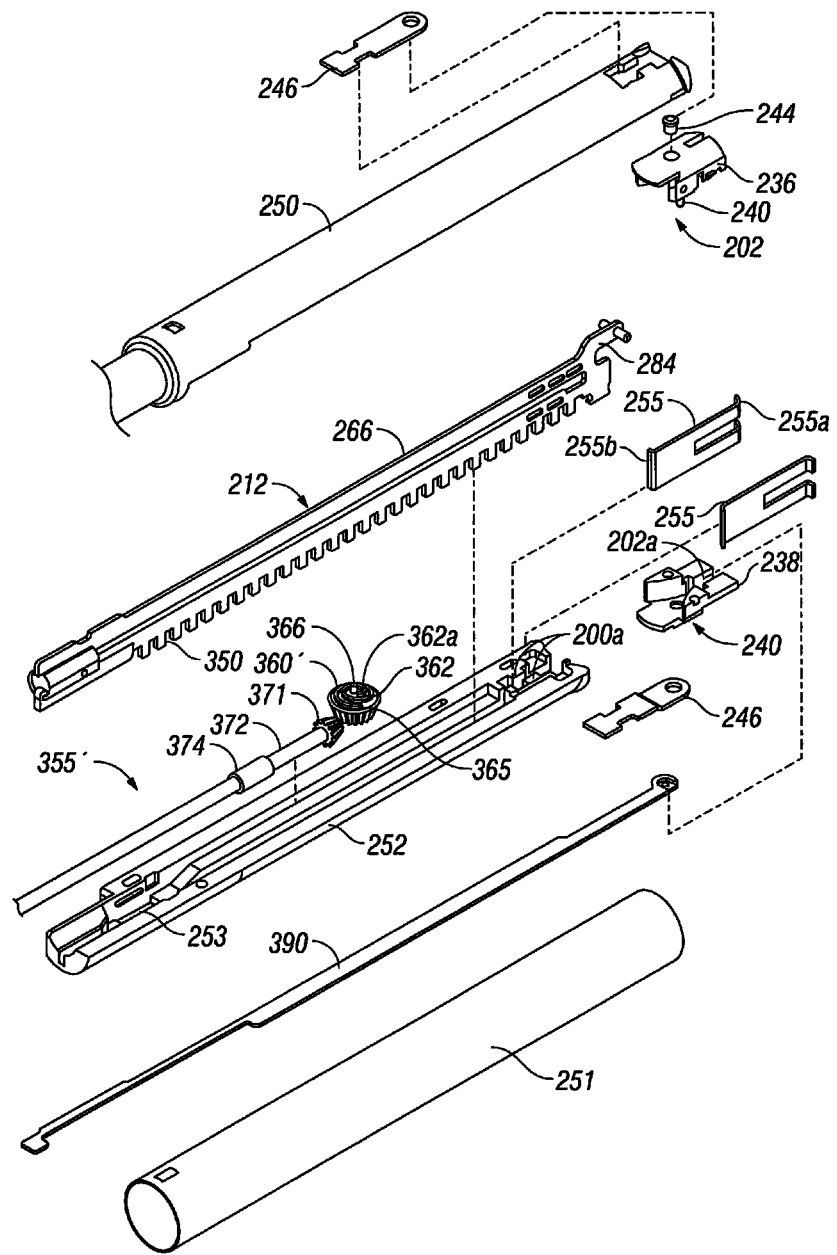
FIG. 16 is an enlarged perspective view with parts separated of the proximal housing portion and mounting assembly of a disposable loading unit with an alternative axial drive assembly according to another embodiment of the present disclosure.
Figure 16A:
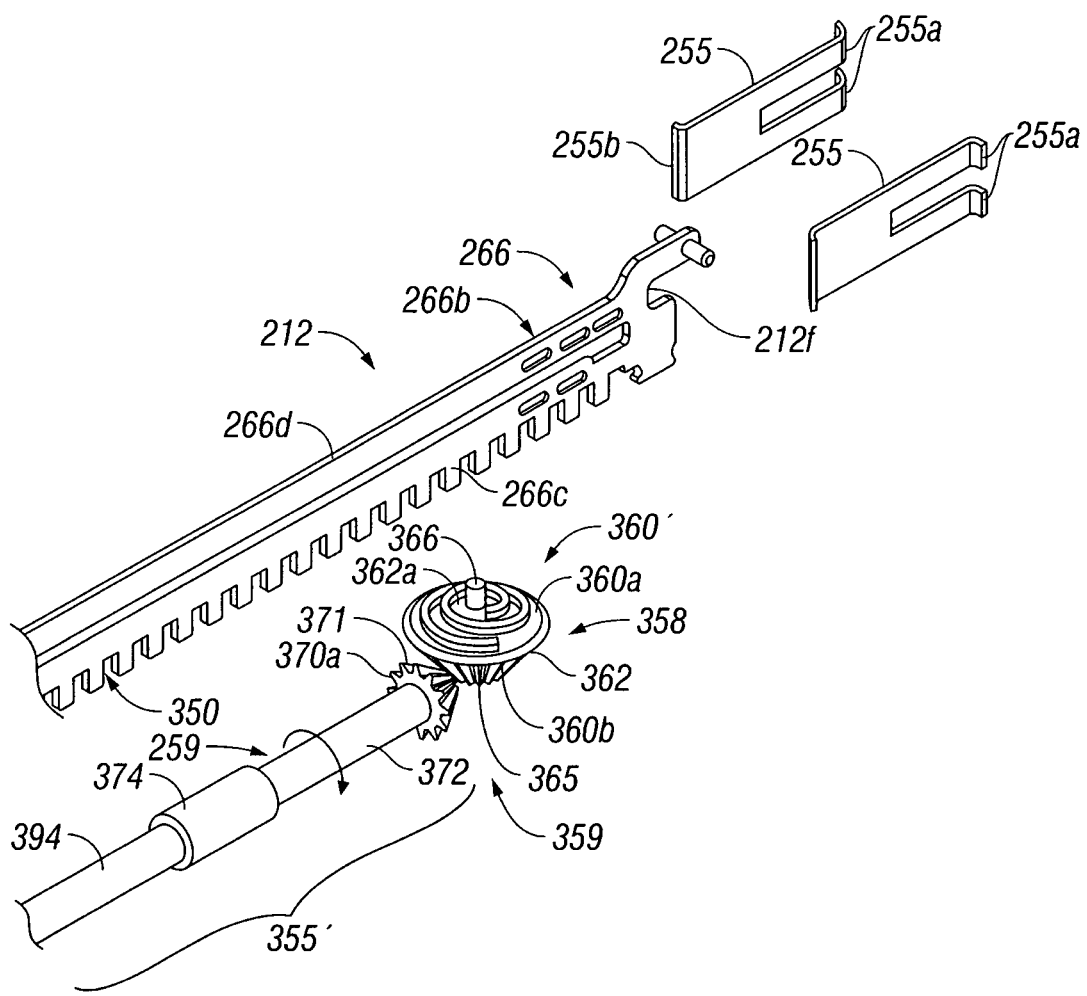
FIG. 16A is a perspective view of the axial drive assembly of FIG. 16 for the disposable loading unit with parts separated.
Figure 16B:
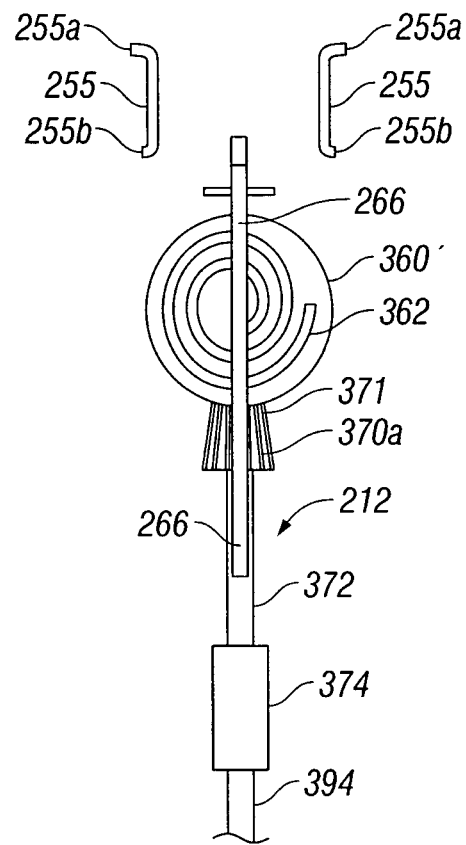
FIG. 16B is a plan view of the axial drive assembly shown in FIG. 16A.
Figure 16C:
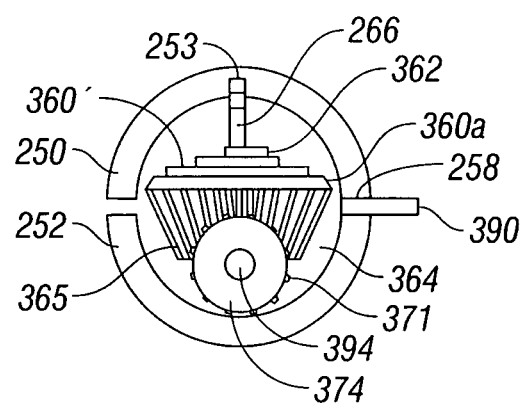
FIG. 16C is a cross-sectional view of the disposable loading unit of FIG. 16.
Figure 17:
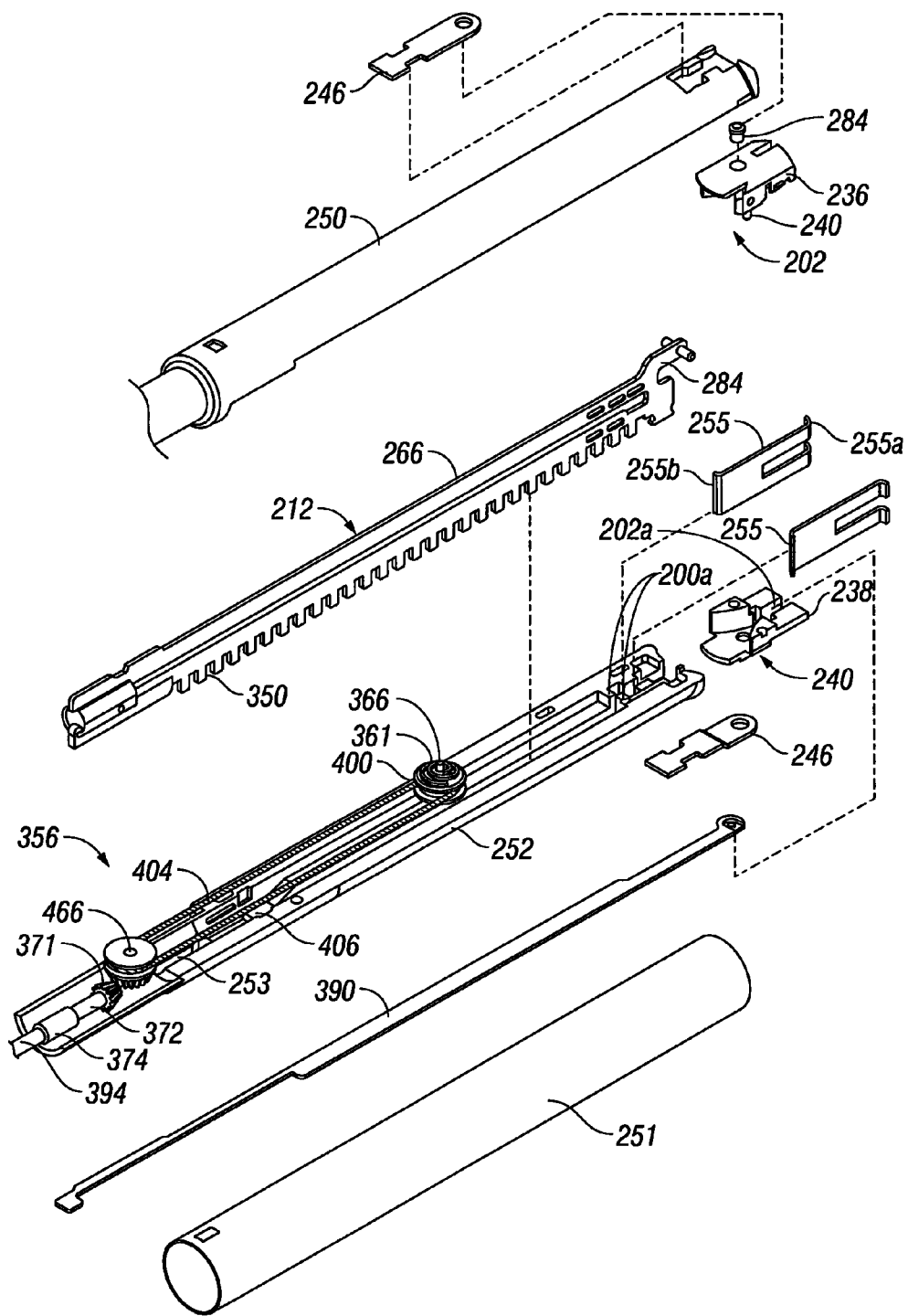
FIG. 17 is an enlarged perspective view with parts separated of the proximal housing portion and mounting assembly of a disposable loading unit with another alternative axial drive assembly according to a further embodiment of the present disclosure.
Figure 17B:
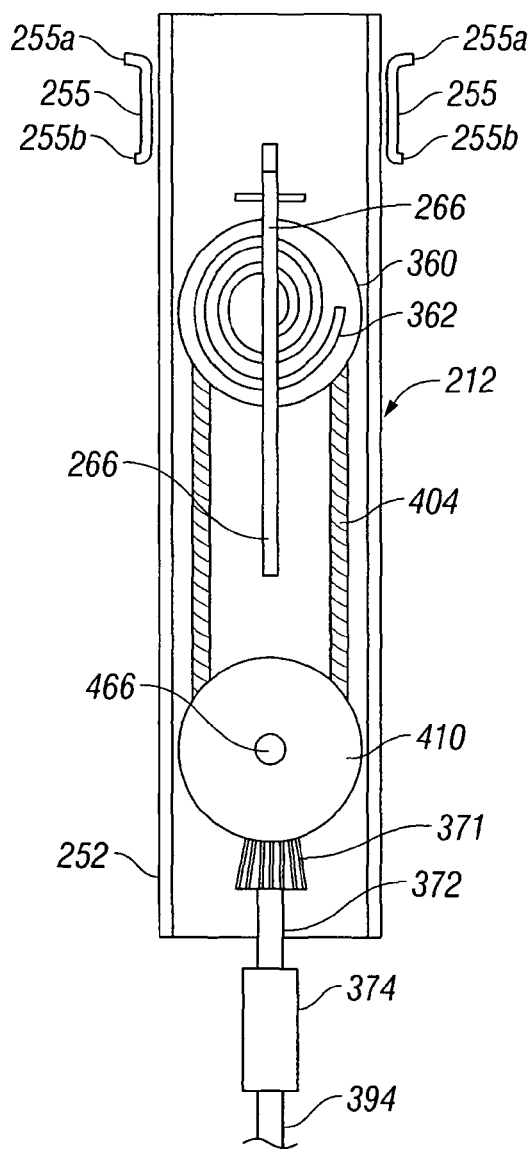
FIG. 17B is a plan view of the axial drive assembly shown in FIG. 17A.
Figure 17C:
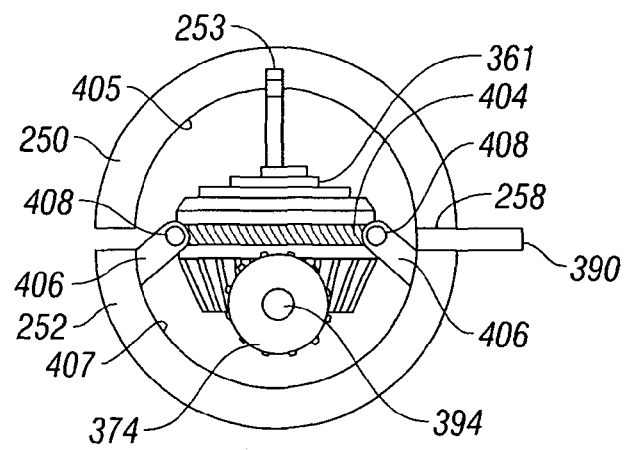
FIG. 17C is a cross-sectional view of the disposable loading unit of FIG. 17.
Figure 18:
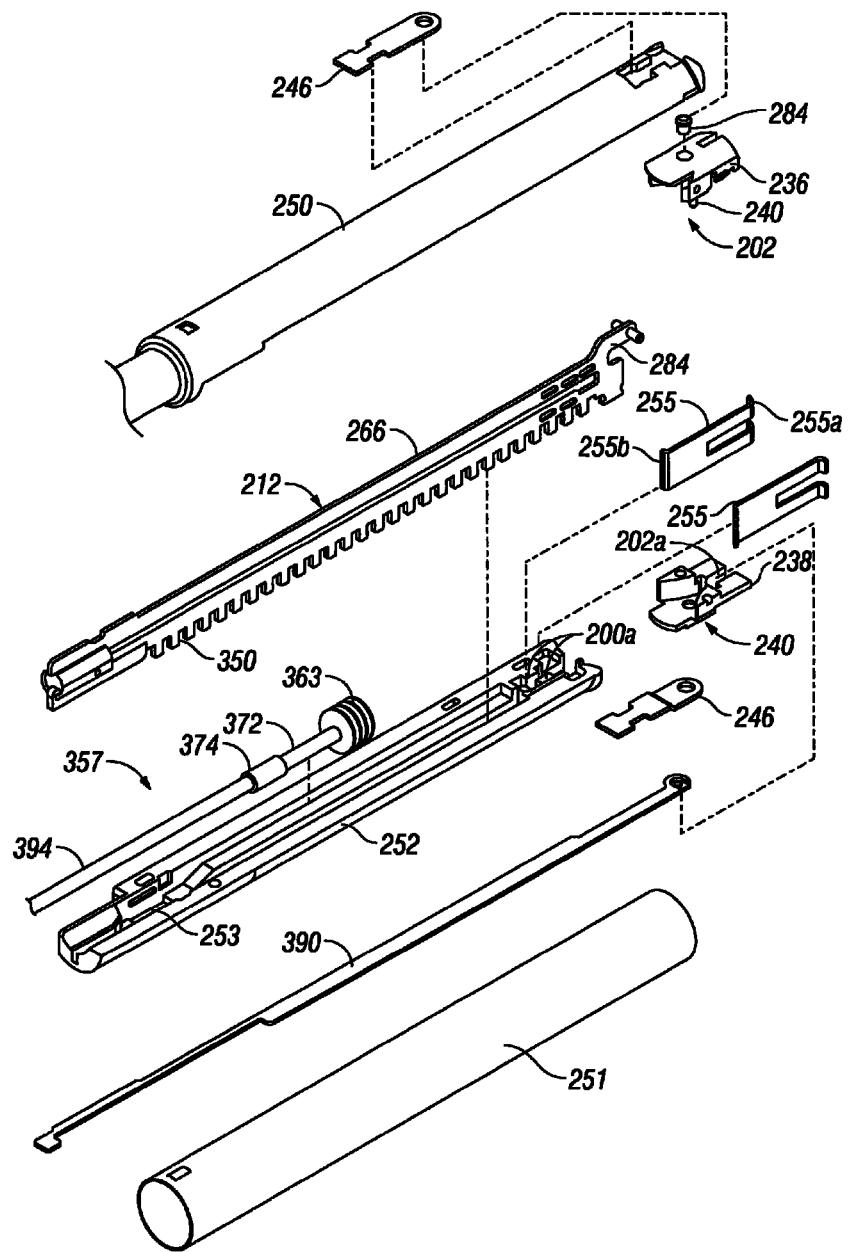
FIG. 18 is an enlarged perspective view with parts separated of the proximal housing portion and mounting assembly of a disposable loading unit with yet another alternative axial drive assembly according to another embodiment of the present disclosure.
Figure 18A:
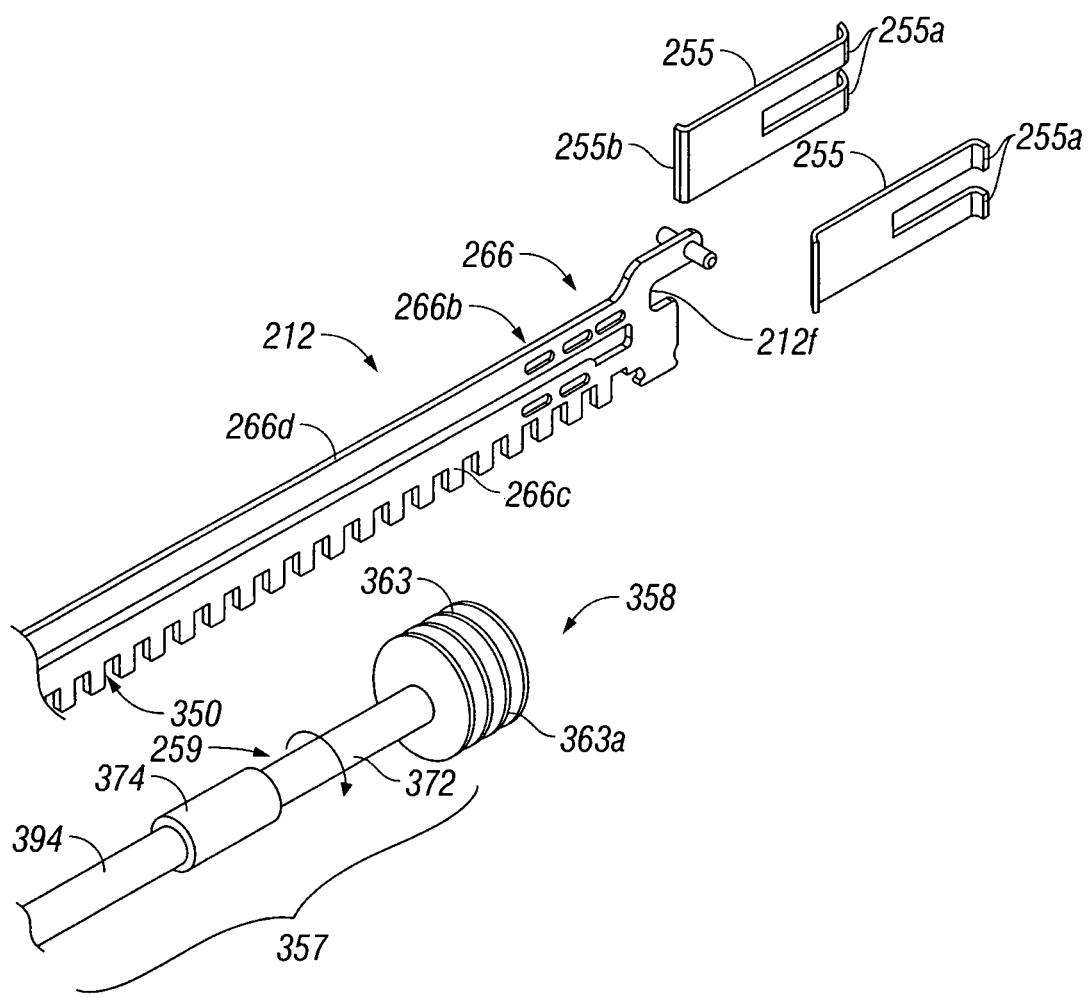
FIG. 18A is a perspective view of the axial drive assembly of FIG. 18 for the disposable loading unit with parts separated.
Figure 18B:
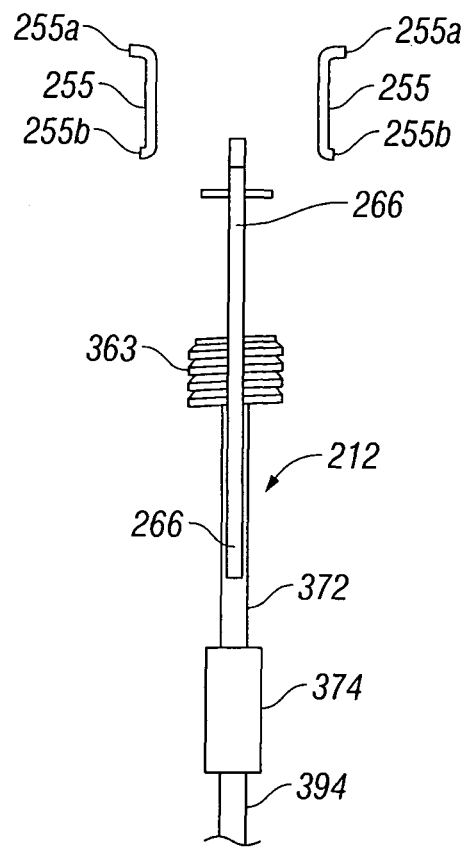
FIG. 18B is a plan view of the axial drive assembly shown in FIG. 18A.
Figure 18C:
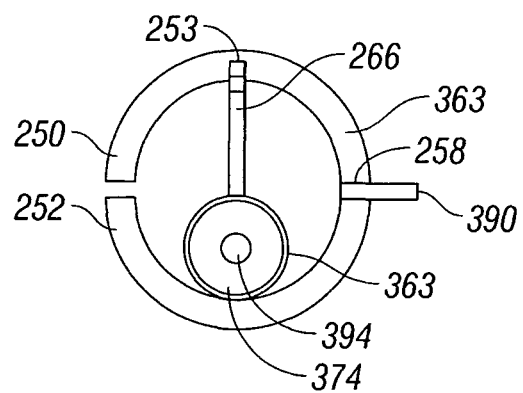
FIG. 18C is a cross-sectional view of the disposable loading unit of FIG. 18.

Elongate body 14 includes housing halves 250 and 252 that define a channel 253 for slidably receiving axial drive assembly 212. The articulation bar 390 is dimensioned to be slidably positioned within a slot 258 formed between housing halves 250 and 252. A pair of blow out plates 255 are positioned adjacent the mounting assembly 202, adjacent the flexible axial drive assembly 212 to prevent or inhibit outward bulging of flexible axial drive assembly 212 during articulation of tool assembly 17. Each blow-out plate 255, for example as illustrated in FIG. 14, includes a planar surface which is substantially parallel to the pivot axis of tool assembly 17 and is positioned on a side of flexible axial drive assembly 212 and the pivot axis to prevent or inhibit outward bulging of flexible axial drive assembly 212. Each blow-out plate 255 includes a first distal bend 255a which is positioned in a respective first groove 202a formed in mounting assembly 202 and a second proximal bend 255b which is positioned in a respective second groove 200a formed in a distal end of housing portion 200. Cover tube 251 encloses housing portion 200.

Referring to FIGS. 14, 14A, 14B and 14C, the surgical stapling apparatus 10 includes the flexible axial drive assembly 212. In one embodiment, the flexible axial drive assembly 212 includes an elongated flexible knife drive beam 266 having a proximal end 266a and a distal end 266b, with a knife blade 280 disposed at the distal end 266b. The flexible knife drive beam 266 has a lower edge 266c and an upper edge 266d and is configured with a plurality of gear teeth 350 disposed in a linear array on the lower edge 266c. The flexible axial drive assembly 212 further includes a gear drive assembly 355.

The gear drive assembly 355 includes a primary drive gear 358 that is configured to mesh with the plurality of gear teeth 350 of the flexible knife drive beam 266. In one embodiment, the primary drive gear 358 may be a crown gear 360 having first and second opposing surfaces 360a and 360b, respectively. The crown gear 360 includes on first surface 360a an ascending spiral cam 362 that ascends from the outer perimeter of the crown gear 360 to an apex 362a disposed generally at the center of the crown gear 360 proximate to a support shaft 366. The crown gear 360 is configured such that the ascending spiral cam 362 meshes with the knife drive beam gear teeth 350. The crown gear 360 includes the support shaft 366 centrally disposed therein defining an axis of rotation of the crown gear 360 wherein rotation of the crown gear 360 around the support shaft 366 causes the ascending spiral cam 362 to rotate, advancing or retracting the flexible knife drive beam 266 as flexible knife drive beam 266 moves along the channel 253. The support shaft 366 may be operatively coupled to the lower housing half 252.

The second or opposing surface 360b includes gear teeth 364 that are configured to mesh with a secondary drive gear 359. In one embodiment, the secondary drive gear 359 is a pinion gear 370. The pinion gear 370 is operatively coupled to the inner rotatable shaft 372 that serves as a gear drive shaft, as explained in more detail below. The teeth 370a of the pinion gear 370 mesh with the gear teeth 364 of the crown gear 360 such that rotation of the pinion gear 370 by the gear drive shaft 372 causes rotation of the crown gear 360 around the axis of rotation of the support shaft 366 in a direction generally orthogonal to the rotation of the pinion gear 370 around the gear drive shaft 372.

As described above with respect to FIGS. 4, 7 and 14, as trigger 116 is squeezed, teeth 117 engage teeth 119 of trigger gear 123 to rotate driver gear 151, which, in turn, rotates first bevel gear 153 which, in turn, rotates bevel drive gear 155. The rotation of the bevel drive gear 155 causes rotation of the inner shaft 394 that is interlocked with gear drive shaft 372 via at least one bearing structure 374 and thus effects rotation of the gear drive shaft 372 and advancement or retraction of the knife drive beam 266.

The gear drive shaft 372 may be supported by at the least one bearing structure 374, e.g., a sleeve bearing or roller bearings, and to enable rotation of the pinion gear 370. The bearing structure 374 supports the gear drive shaft 372 such that the drive shaft 372 generally resides in the vicinity of the inner surface of lower housing half 252. The bearing structure 374 may be disposed on the lower housing half 252. The upper housing half 250 defines a channel 253 for slidably receiving the knife drive beam 266 via the upper edge 266d.

In one embodiment, as illustrated in FIGS. 16 and 16A-16C, the gear drive assembly 355 (see FIGS. 14 and 14A-14C) may be substituted by a gear drive assembly 355'. Gear drive assembly 355' is identical to gear drive assembly 355 with the exception that primary drive gear 358 now includes a crown gear 360'. In comparison to crown gear 360, crown gear 360' also has first and second opposing surfaces 360a and 360b, respectively. The crown gear 360' includes on first surface 360a the spiral cam 362 that ascends from the outer perimeter of the crown gear 360' to the apex 362a disposed generally at the center of the crown gear 360' proximate to the support shaft 366. The crown gear 360' is configured also such that the ascending spiral cam 362 meshes with the knife drive beam gear teeth 350 wherein rotation of the crown gear 360' around the support shaft 366 causes the ascending spiral cam 362 to at least one of advance or retract the knife drive beam 266 as knife drive beam 266 moves along the channel 253. Again, the support shaft 366 may be operatively coupled to the lower housing half 352.

However, in contrast to crown gear 360, crown gear 360' includes around the periphery miter gear teeth 365 that are configured to mesh with secondary drive gear 359 wherein secondary drive gear 359 is now a miter gear 371 disposed at the distal end of gear drive shaft 372. The crown gear 360' includes support shaft 366 centrally disposed therein defining an axis of rotation of the crown gear 360' and disposed such that rotation of the miter gear 371 by the gear drive shaft 372 causes rotation of the crown gear 360' around the axis of rotation of the support shaft 366 in a direction generally orthogonal to the rotation of the miter gear 371 around the gear drive shaft 372.

In one embodiment, as illustrated in FIGS. 17 and 17A-17C, the gear drive assembly 355 (see FIGS. 14 and 14A-14C) or 355' (see FIGS. 16 and 16A-16C) may be substituted by a gear drive assembly 356. Gear drive assembly 356 is similar to gear drive assemblies 355 and 355' except that gear drive assembly 356 includes as primary drive gear 358 a crown gear 361 instead of crown gears 360 and 360'. The crown gear 361 also includes first and second opposing surfaces 360a and 360b, respectively. The crown gear 361 includes on first surface 360a the spiral cam 362 that ascends from the outer perimeter of the crown gear 361 to the apex 362a disposed generally at the center of the crown gear 361 proximate to the support shaft 366. The crown gear 361 is configured also such that the ascending spiral cam 362 meshes with the knife drive beam gear teeth 350 wherein rotation of the crown gear 361 around the support shaft 366 causes the ascending spiral cam 362 to at least one of advance or retract the knife drive beam 266 as knife drive beam 266 moves along the channel 253. Similarly, the support shaft 366 may be operatively coupled to the lower housing half 252.

However, in contrast to crown gear 360' that includes around the periphery miter gear teeth 365 that are configured to mesh with the secondary drive gear 359, crown gear 361 includes on second surface 360b a first pulley 400 having a diameter which may extend to the periphery of the crown gear 361. The first pulley 400 includes a circumferential channel 402 formed around the periphery.

In one embodiment, the gear drive assembly 356 may include a second pulley 410 having first and second opposing surfaces 410a and 410b and a support shaft 466 centrally disposed therein is disposed on the lower housing half 252, and defining the axis of rotation of the pulley 410. The support shaft 466 may also be operatively coupled to the lower housing half 252 at the proximal end of the knife drive beam 266. The second pulley 410 includes a circumferential channel 412 formed around the periphery. In a manner similar to crown gear 360' (see FIG. 16A), the second pulley 410 further includes around the periphery of lower surface 400a the plurality of miter teeth 365 that are configured to mesh with the secondary drive gear 359 wherein secondary drive gear 359 is again miter gear 371 disposed at the distal end of gear drive shaft 372.

As described above, the second pulley 410 includes the support shaft 466 centrally disposed therein and defining an axis of rotation of the pulley 410 and disposed such that rotation of the miter gear 371 by the gear drive shaft 372 causes rotation of the pulley 410 around the axis of rotation of the support shaft 466 in a direction generally orthogonal to the rotation of the miter gear 371 around the gear drive shaft 372.

The first and second pulleys 400 and 410, respectively, may be operatively coupled to one another via a common closed cable loop 404 that is disposed in the channels 402 and 412 such that rotation of the second pulley 410 via rotation of the gear drive shaft 372 effects rotation of the first pulley 400, and crown gear 361 thereby, via the closed cable loop 404. To maintain the configuration of the first and second pulleys 400 and 410, respectively, and the cable loop 404 coupled therebetween, referring to FIG. 17C, channel support structures 406 may be disposed on the inner surface 407 of the lower housing half 252. The channel support structures 406 include channels 408 formed therethrough and configured to restrain and guide the cable loop 404 while enabling free rotation thereof. In further embodiments, the second pulley 410 is located in the housing assembly 112, which includes support structures for the second pulley 410 and cable loop 404.

In the same manner as described previously, rotation of the crown gear 361 around the support shaft 366 causes the ascending spiral cam 362 to at least one of advance or retract the knife drive beam 266 as knife drive beam 266 moves along the channel 253.

In one embodiment, in conjunction with FIGS. 18 and 18A-18C, the gear drive assembly 355 (see FIGS. 14 and 14A-14C) may be substituted by a gear drive assembly 357. Gear drive assembly 357 is similar to gear drive assembly 355 with the exception that primary drive gear 358 is now a worm gear 363, in contrast to crown gear 360. No secondary drive gear is required for gear drive assembly 357. Teeth 363a of the worm gear 363 are oriented and configured to mesh with the knife drive beam gear teeth 350 wherein rotation of the worm gear 363 by the gear drive shaft 372 causes at least one of advancement and retraction of the knife drive beam 266 as knife drive beam 266 moves along the channel 253.

One of ordinary skill in the art will recognize that other gear drive assemblies may be conceived or applied to effect the advancement and retraction of the knife drive beam 266. The embodiments are not limited to the gear drive assemblies discussed above.

In addition, one of ordinary skill in the art will recognize that the flexible axial drive assembly 212 may be configured such that the gear teeth 350 may be disposed on the upper edge 266d of the flexible knife drive beam 266 and the primary drive gear 358 and secondary drive gear 359 arranged accordingly with respect to the upper housing half 250 rather than the lower housing half 252. The embodiments are not limited to gear teeth disposed on the lower edge of the knife drive beam.

The arrangement and configuration of the gear drive assembly 355 having crown gear 360 with the ascending spiral cam 362 advancing or retracting the flexible knife drive beam 266 provides an overall mechanical advantage in the range of about 60 to 1 in terms of reduced exertion force and increased travel time for the flexible knife drive beam 266. (By way of example, the mechanical advantage of the combination of the pinion gear 370 to crown gear 360 may be about 3 to 1, while the mechanical advantage of the combination of the ascending spiral cam 362 to the flexible knife drive beam 266 may be about 20 to 1). The resulting reduced exertion force and increased travel time for the flexible knife drive beam 266 tends to substantially reduce the probability of bulging out (or buckling) of the flexible axial drive assembly 212 that may occur during articulation of tool assembly 17.

Articulation of the tool assembly 17 may be effected by various means known to or conceivable by those skilled in the art, as one example disclosed by Milliman et al. in U.S. Pat. No. 6,953,139 referenced above, and hereby incorporated by reference herein. More particularly, referring to FIG. 19, cam member 136 includes a housing 144 having an elongated slot 146 extending through one side thereof and a stepped camming surface 148 formed in the other side thereof. Each step 340 of camming surface 148 corresponds to a particular degree of articulation of stapling apparatus 10. Although three steps are illustrated, fewer or more steps may be provided.

Figure 5:
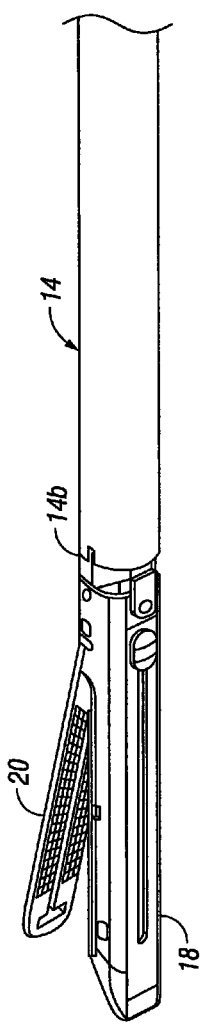
FIG. 5 is a perspective view of an articulating disposable loading unit for the surgical apparatus shown in FIG. 1.
Figure 6:
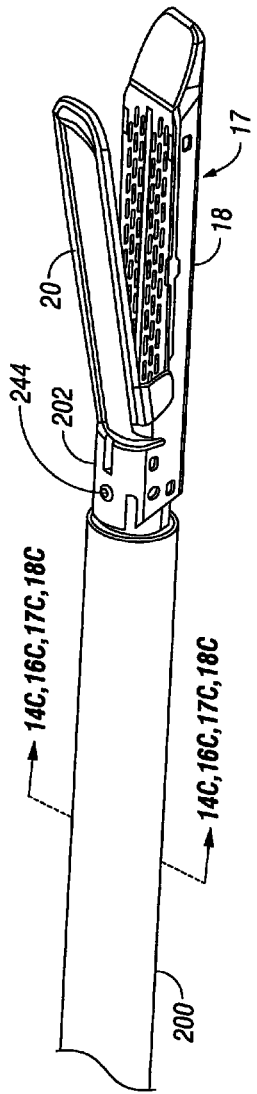
FIG. 6 is a perspective view of a disposable loading unit usable with the surgical apparatus of FIG. 1.
Figure 7:
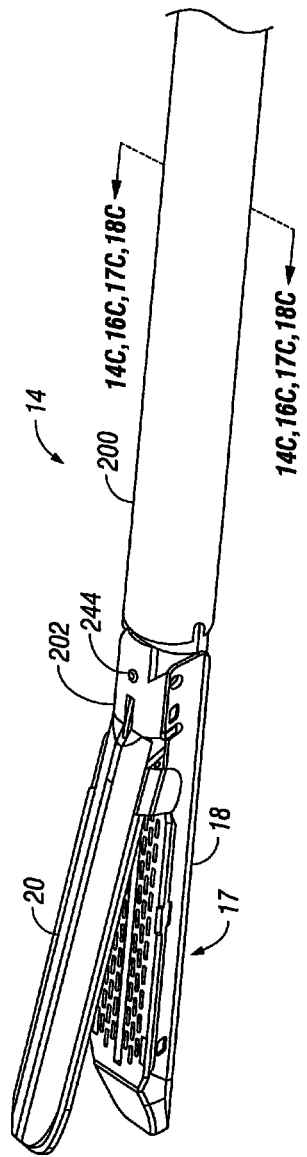
FIG. 7 is another perspective view of a disposable loading unit usable with the surgical apparatus of FIG. 1.
Figure 8:
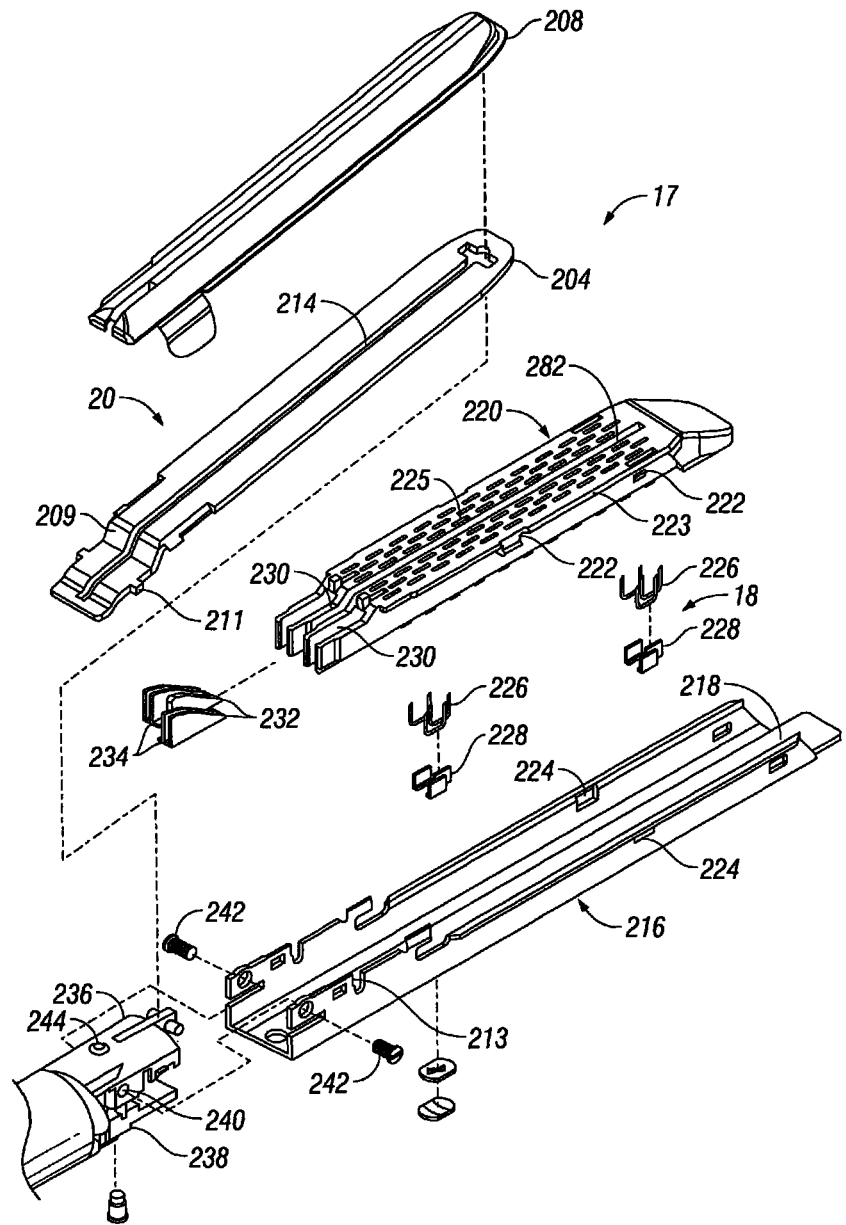
FIG. 8 is an exploded perspective view of the tool assembly of the surgical apparatus of FIG. 1 with parts separated.
Figure 9:
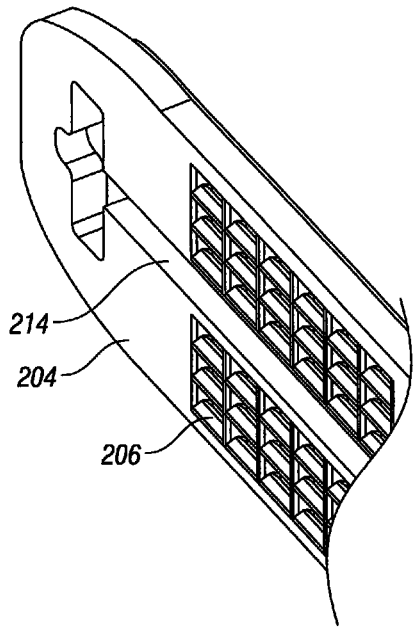
FIG. 9 is an enlarged partial perspective view of the distal end of the anvil assembly of the surgical apparatus of FIG. 1 showing a plurality of staple deforming cavities.
Figure 10:
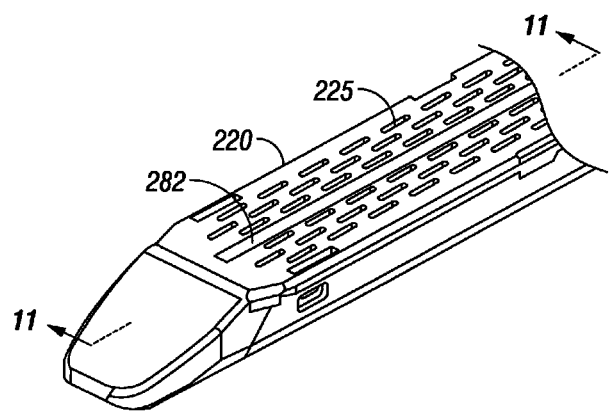
FIG. 10 is an enlarged partial perspective view of the distal end of the staple cartridge of the surgical apparatus shown in FIG. 1.
Figure 11:
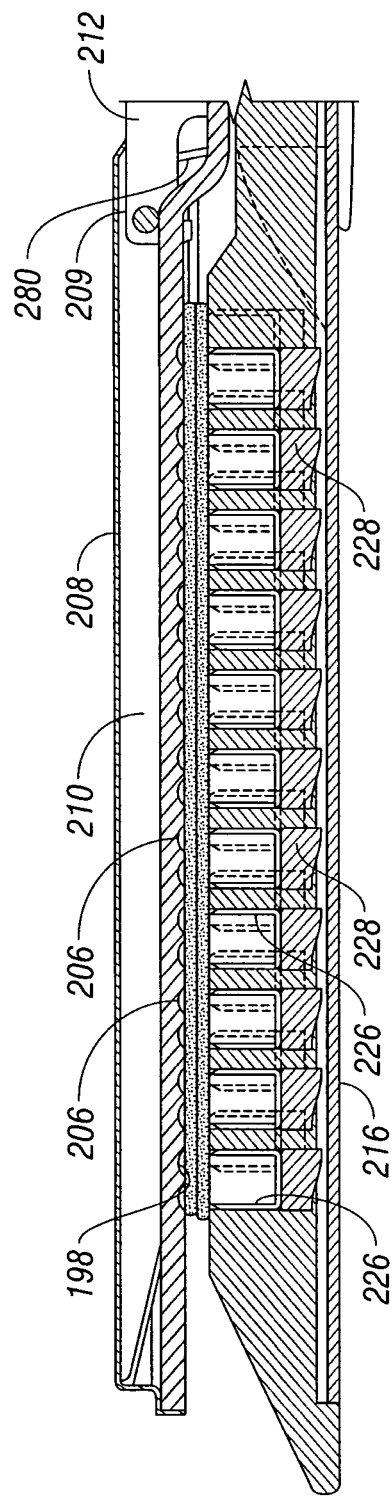
FIG. 11 is a side cross-sectional view taken along section line 11-11 of FIG. 10.
Figure 12:
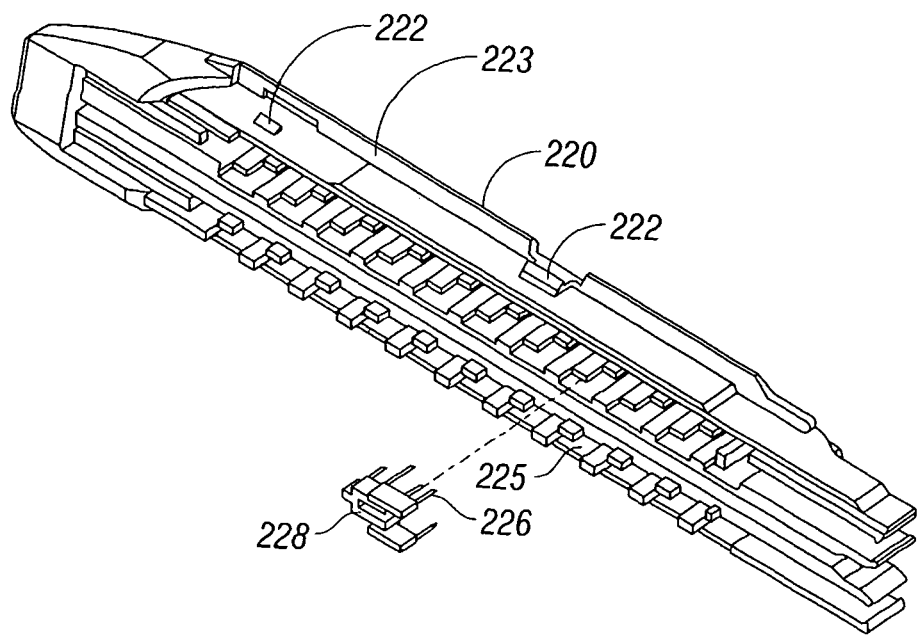
FIG. 12 is a bottom perspective view of the staple cartridge shown in FIG. 8.
Figure 13:
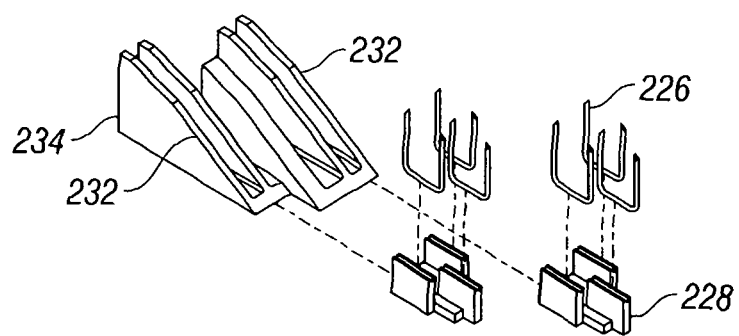
FIG. 13 is an enlarged perspective view of the actuation sled, the pushers and the fasteners shown in FIG. 8.
Figure 19:
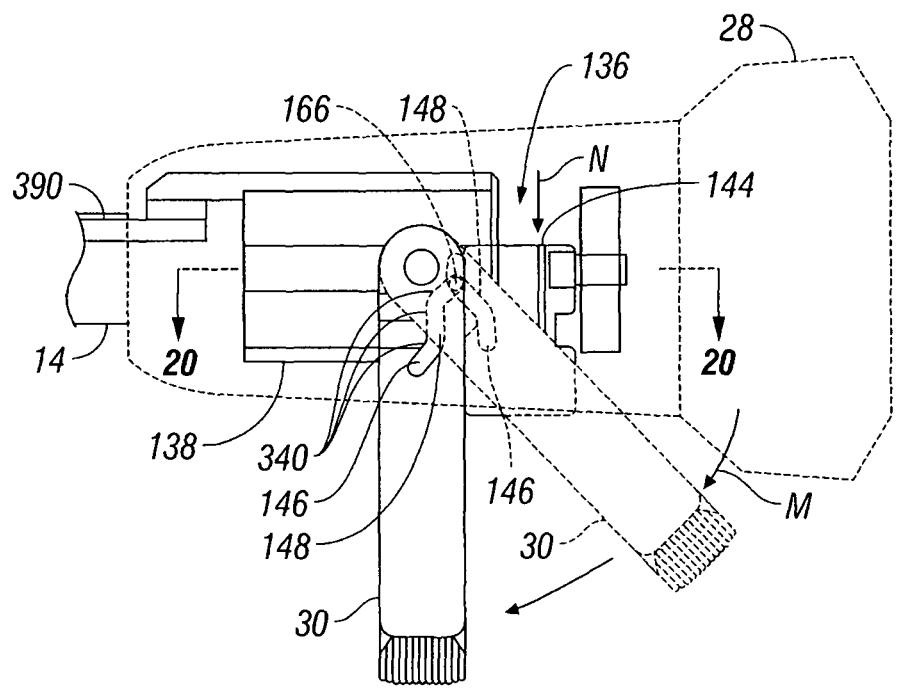
FIG. 19 is a top view of the articulation mechanism of the surgical apparatus of FIG. 1.
Figure 20:
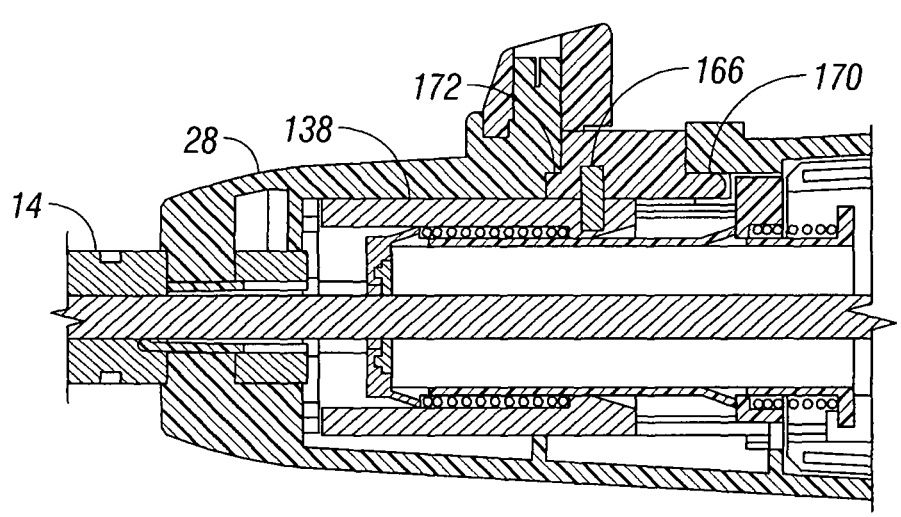
FIG. 20 is a side cross-sectional view of the articulation mechanism and rotation member of the surgical apparatus shown in FIG. 1.

In conjunction with FIGS. 5 and 19, referring also to FIGS. 20-25, when articulation lever 30 is pivoted in the direction indicated by arrow "M" in FIG. 19, cam member 136 is moved transversely in the direction indicated by arrow "N" between flanges 170 and 172 of rotation knob 28.

Figure 21:
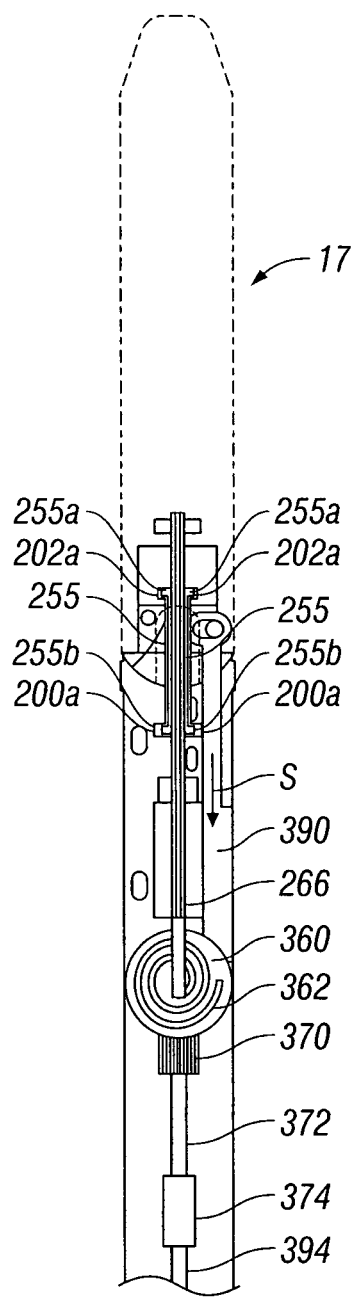
FIG. 21 is a top view of the distal end of the surgical apparatus shown in FIG. 1, during articulation of the tool assembly.
Figure 23:
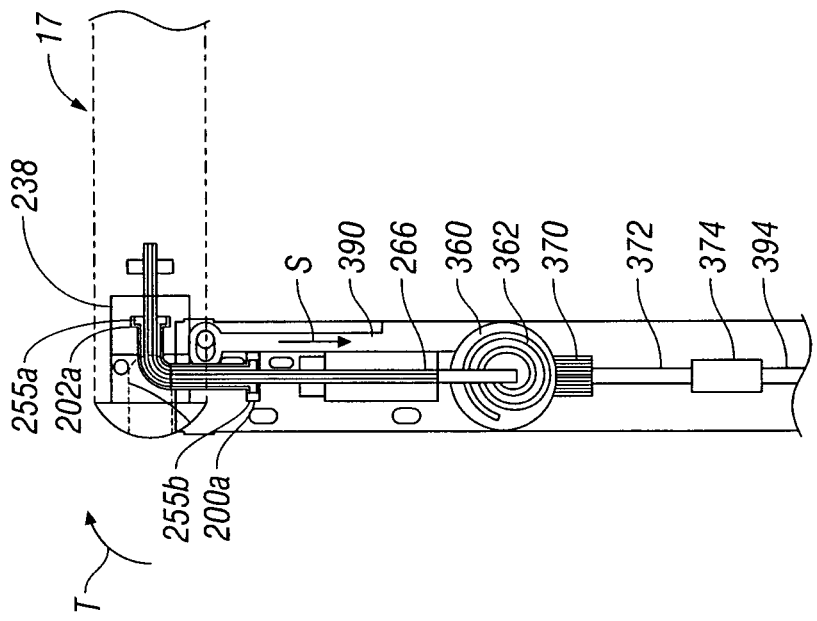
FIG. 23 is a top view of the distal end of the surgical apparatus shown in FIG. 1 during articulation of the tool assembly.
Figure 22:
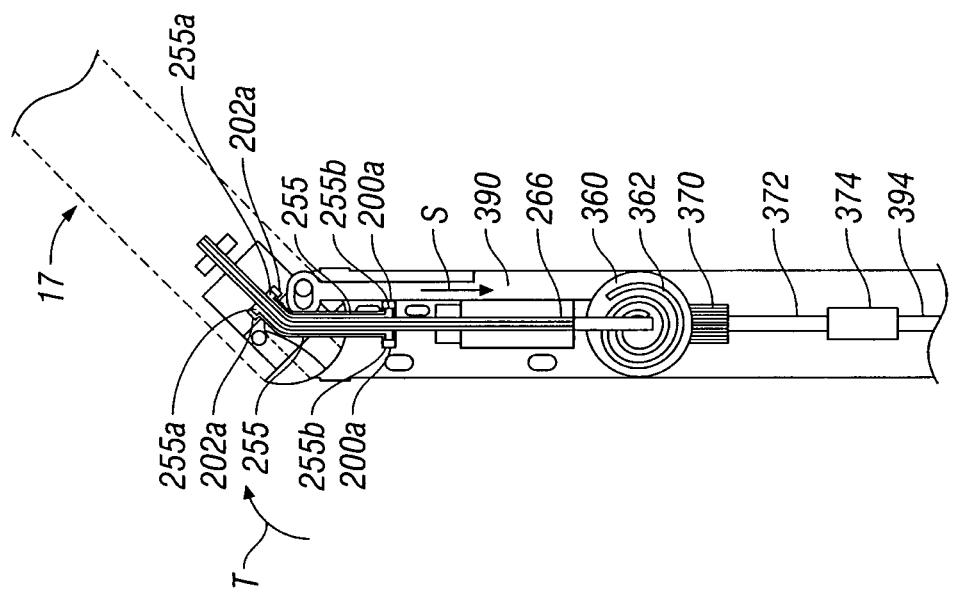
FIG. 22 is a top view of the distal end of the surgical apparatus shown in FIG. 1 during articulation of the tool assembly.
Figure 24:
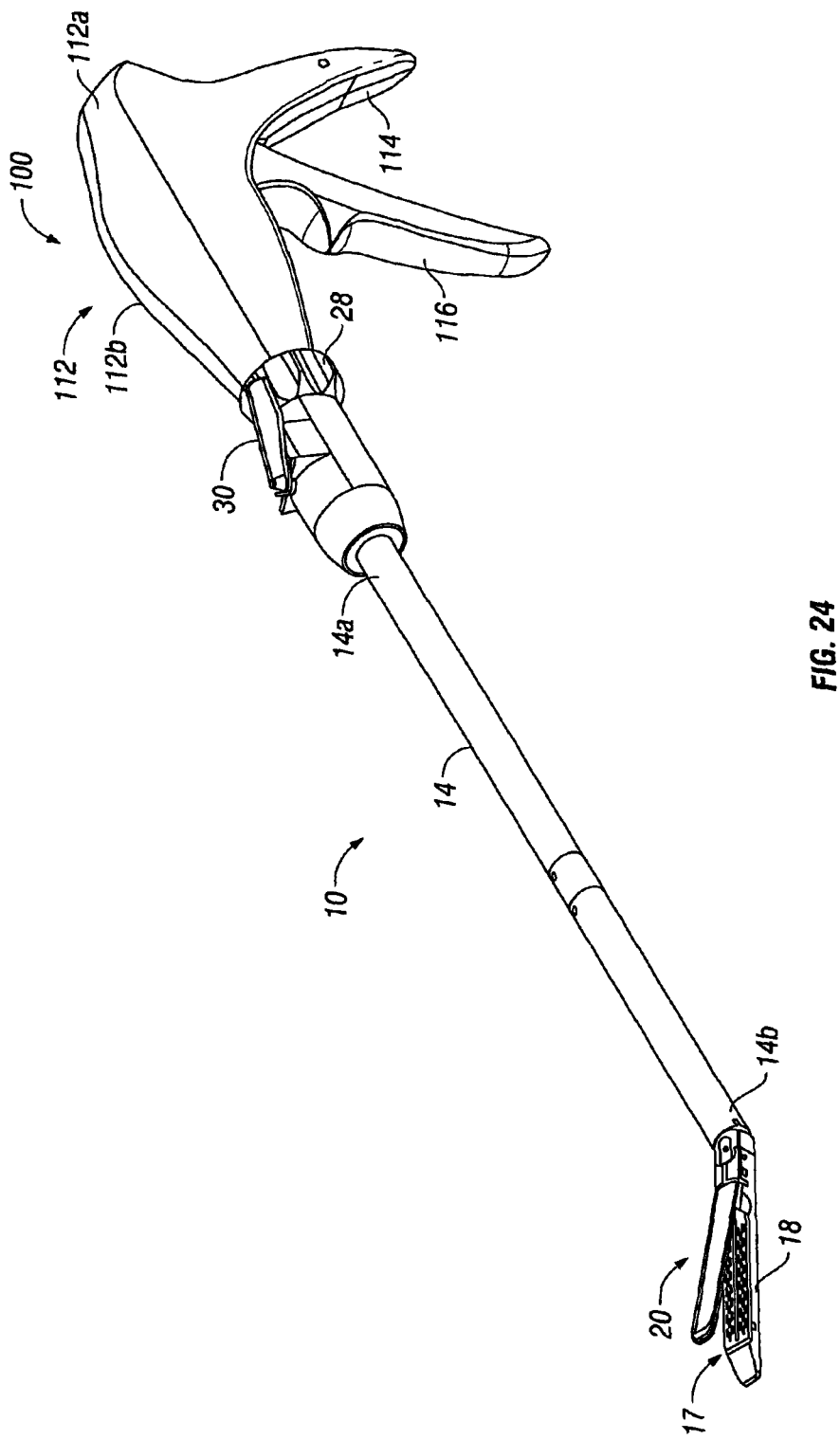
FIG. 24 is a perspective view of the surgical apparatus shown in FIG. 1, with the tool assembly articulated in a first direction.
Figure 25:
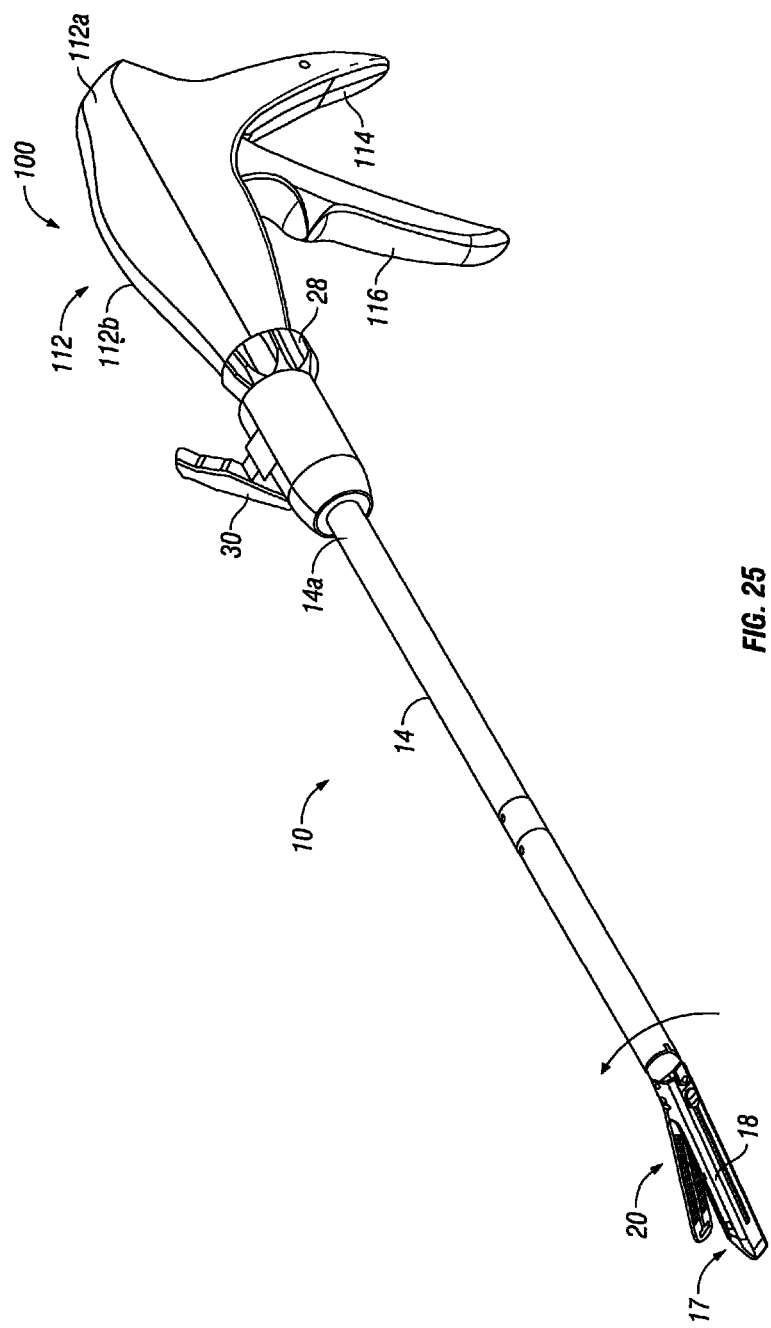
FIG. 25 is a perspective view of the surgical apparatus shown in FIG. 1, with the tool assembly articulated in a second direction.

FIGS. 21-23 illustrate articulation of tool assembly 17 in a direction so as to cause a longitudinal axis of the tool assembly 17 to deviate from a longitudinal axis of the elongate body 14. The articulation bar 390 is attached to the mounting assembly 202 (see FIG. 6) at a location off-set from the longitudinal axis of the tool assembly 17. When articulation bar 390 is retracted by rotating articulation lever 30 in a counter-clockwise direction (not shown) as viewed in FIG. 19, pin 166 is forced to move proximally along stepped camming surface 148, moving translation member 138 and articulation bar 390 proximally. Movement of articulation bar 390 proximally, as indicated by arrow "S" in FIGS. 22-23, rotates tool assembly 17 in a single direction such as a clockwise direction, as indicated by arrow "T" in FIGS. 22-23. Advancement of the articulation bar 390 in a distal direction pivots the tool assembly 17 in the opposite direction.

Referring to FIG. 19, movement of pin 166 between adjacent step portions 340 causes tool assembly 17 to articulate and knife drive beam 266 to bend correspondingly, as indicated in FIG. 22. Additional movement of pin 166 to the next adjacent step portion 340 causes tool assembly 17 to articulate further and knife drive beam 266 to bend further as indicated in FIG. 23. Those skilled in the art will recognize that knife drive beam 266 is made from a flexible engineering material such as plastic or metal.

In certain embodiments, the surgical stapling apparatus 10 includes a second articulation bar and a first articulation bar. The first articulation bar is disposed on a first side of the pivot axis of the tool assembly and the second articulation bar is disposed on the opposite side of the pivot axis.

Consequently, in the stapling apparatus 10 according to the present disclosure, the flexible axial drive assembly 212 includes one of the gear drive assemblies discussed above to advance and retract the flexible knife drive beam 266 in a manner providing a mechanical advantage that substantially reduces the exertion force and increases the travel time to extend and retract the flexible knife drive beam 266, correspondingly substantially reducing the probability of bulging out or buckling of the flexible axial drive assembly 212 while at the same time providing the capability of at least one-directional articulation to about 90 degrees of bending of the flexible knife drive beam 266.

In view of the foregoing, the surgical stapling apparatus 10 includes the handle assembly 100, the elongated body portion 14 extending distally from the handle assembly 100 and defining a first longitudinal axis. The surgical stapling apparatus 10 also includes the tool assembly 17 pivotally supported on the distal end of the elongated body portion 17 about a pivot axis substantially orthogonal to the first longitudinal axis, the tool assembly 17 defining a second longitudinal axis and being movable between a first position in which the second longitudinal axis is aligned with the first longitudinal axis to a second position in which the second longitudinal axis is positioned at an angle to the first longitudinal axis. The surgical stapling apparatus also includes the flexible axial drive assembly 212 that includes the flexible knife drive beam 266 extending from a position proximal of the pivot axis to a position distal of the pivot axis, with the flexible knife drive beam 266 having a distal end which is movable in relation to the tool assembly 17 to actuate the tool assembly 17 and a gear drive assembly, e.g., gear drive assemblies 355, 355', 356, or 357, interfacing with the flexible knife drive beam 266 to enable movement of the distal end of the flexible knife drive beam 266 in relation to the tool assembly 17.

The movement of the distal end of the flexible knife drive beam 266 in relation to the tool assembly 17 may be effected independently of the movement of the tool assembly 17 between the first position in which the second longitudinal axis is aligned with the first longitudinal axis to the second position in which the second longitudinal axis is positioned at an angle to the first longitudinal axis.

It can be appreciated that although the various embodiments of surgical stapling apparatus 10 having gear driven knife drive mechanisms according to the present disclosure have been illustrated and described with respect to an articulating surgical stapling apparatus, those skilled in the art will recognize that the gear driven knife drive mechanisms according to the present disclosure may be applied to a non-articulating surgical stapling apparatus. The embodiments are not limited to articulating surgical stapling apparatuses.

Although the subject disclosure has been described with respect to exemplary embodiments, it will be readily apparent to those having ordinary skill in the art to which it appertains that changes and modifications may be made thereto without departing from the spirit or scope of the subject invention as defined by the appended claims.

What is claimed is:

1. A surgical apparatus comprising:
    a handle assembly;
    an elongated body portion extending distally from the handle assembly and defining a first longitudinal axis;
    a tool assembly pivotally supported on the distal end of the elongated body portion about a pivot axis substantially orthogonal to the first longitudinal axis, the tool assembly defining a second longitudinal axis and being movable between a first position in which the second longitudinal axis is aligned with the first longitudinal axis to a second position in which the second longitudinal axis is positioned at an angle to the first longitudinal axis; and
    a flexible axial drive assembly including:
        a flexible knife drive beam extending from a position proximal of the pivot axis to a position distal of the pivot axis, the flexible knife drive beam having a distal end which is movable in relation to the tool assembly to actuate the tool assembly, wherein the flexible knife drive beam at least one of advances and retracts at a distal end thereof to effect the axial movement of the flexible knife drive beam in relation to the tool assembly; and
        a gear drive assembly disposed within the elongated body portion and operatively coupled to the flexible knife drive beam to effect axial movement of the distal end of the flexible knife drive beam in relation to the tool assembly, the gear drive assembly including a primary drive gear meshing with the flexible knife drive beam to effect the movement of the flexible knife drive beam, wherein the primary drive gear is a primary drive crown gear having first and second opposing surfaces, the primary drive crown gear including a support shaft centrally disposed therein defining an axis of rotation of the primary drive crown gear, the primary drive crown gear including on the first surface a spiral cam, the primary drive crown gear being configured such that the spiral cam meshes with the flexible knife drive beam wherein rotation of the primary drive crown gear around the support shaft causes the spiral cam to at least one of advance and retract the flexible knife drive beam to effect the axial movement of the distal end thereof.

2. A surgical apparatus according to claim 1, wherein the movement of the distal end of the flexible knife drive beam in relation to the tool assembly is effected independently of the movement of the tool assembly between the first position in which the second longitudinal axis is aligned with the first longitudinal axis to the second position in which the second longitudinal axis is positioned at an angle to the first longitudinal axis.

3. A surgical apparatus according to claim 1,
wherein the gear drive assembly further comprises:
a gear drive shaft; and
a secondary drive gear operatively coupled to the gear drive shaft, the secondary drive gear meshing with the primary drive crown gear to effect the rotation of the primary drive crown gear around the support shaft.

4. A surgical apparatus according to claim 3, wherein the primary drive crown gear comprises gear teeth that are configured to mesh with the secondary drive gear.

5. A surgical apparatus according to claim 4, wherein the gear teeth of the primary drive crown gear are disposed on the second surface and configured to mesh with the secondary drive gear, and wherein the secondary drive gear is a pinion gear.

6. A surgical apparatus according to claim 5, wherein the gear teeth of the primary drive crown gear are configured in a miter formation to mesh with the secondary drive gear, and wherein the secondary drive gear is a miter gear.

7. A surgical apparatus according to claim 3, wherein the handle assembly comprises:
a trigger; and
a driver/torque subassembly,
wherein the trigger and the driver/torque subassembly are operatively coupled to effect rotation of the gear drive shaft upon operation of the trigger.

8. A surgical apparatus according to claim 1, wherein the primary drive crown gear further comprises a first pulley and a cable operatively coupled thereto, the first pulley and the cable configured to effect the rotation of the primary drive crown gear around the support shaft.

9. A surgical apparatus according to claim 8, wherein the gear drive assembly further comprises a second pulley operatively coupled to the first pulley via the cable to effect the rotation of the primary drive crown gear around the support shaft.

10. A surgical apparatus according to claim 9, wherein the second pulley further comprises gear teeth and wherein the gear drive assembly further comprises:
a gear drive shaft; and
a secondary drive gear operatively coupled to the gear drive shaft, the secondary drive gear meshing with the gear teeth of the second pulley to effect the rotation of the primary drive crown gear around the support shaft.

11. A surgical apparatus according to claim 10, wherein the handle assembly comprises:
a trigger; and
a driver/torque subassembly,
wherein the trigger and the driver/torque subassembly are operatively coupled to effect rotation of the gear drive shaft upon operation of the trigger.

12. A surgical apparatus according to claim 1, wherein the handle assembly comprises:
a trigger; and
a driver/torque subassembly,
wherein the trigger and the driver/torque subassembly are operatively coupled to effect rotation of the gear drive shaft upon operation of the trigger.

13. A surgical apparatus according to claim 1, wherein the gear drive assembly is configured to provide a mechanical advantage of about 60 to 1.

14. A surgical apparatus according to claim 1, wherein the angle between the first longitudinal axis and the second longitudinal axis is at least forty-five degrees.

15. A surgical apparatus according to claim 14, wherein the angle between the first longitudinal axis and the second longitudinal axis is at least ninety degrees.

16. A surgical apparatus according to claim 1, further comprising:
at least one flexible planar blow out plate having a proximal end positioned on one side of the flexible knife drive beam and extending from a position proximal of the pivot axis to a position distal of the pivot axis, the at least one planar blow out plate having a planar surface substantially parallel to the pivot axis such that the at least one blow-out plate is positioned to inhibit outward bulging of the flexible knife drive beam.

17. A surgical apparatus according to claim 1, wherein the gear drive assembly is disposed in a distal portion of the elongated body portion and is operatively coupled to the flexible knife drive beam to effect axial movement of the distal end of the flexible knife drive beam in relation to the tool assembly.

* * * * *